United States Patent
Horn et al.

(10) Patent No.: US 10,168,321 B2
(45) Date of Patent: Jan. 1, 2019

(54) COMPOSITION COMPRISING UP-CONVERTING PHOSPHORS FOR DETECTING AN ANALYTE

(71) Applicant: Roche Diabetes Care, Inc., Indianapolis, IN (US)

(72) Inventors: Carina Horn, Biblis (DE); Timo-Jaakko Valta, Turku (FI)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 15/163,153

(22) Filed: May 24, 2016

(65) Prior Publication Data

US 2016/0266098 A1 Sep. 15, 2016

Related U.S. Application Data

(63) Continuation of application No. PCT/EP2014/075639, filed on Nov. 26, 2014.

(30) Foreign Application Priority Data

| Nov. 27, 2013 | (EP) | ................................. | 13194585 |
| Mar. 10, 2014 | (EP) | ................................. | 14158504 |
| Jun. 16, 2014 | (EP) | ................................. | 14172572 |

(51) Int. Cl.
| *G01N 33/52* | (2006.01) |
| *G01N 21/77* | (2006.01) |
| *C12Q 1/32* | (2006.01) |
| *C12Q 1/26* | (2006.01) |
| *C12Q 1/54* | (2006.01) |

(52) U.S. Cl.
CPC ............. *G01N 33/525* (2013.01); *C12Q 1/26* (2013.01); *C12Q 1/32* (2013.01); *C12Q 1/54* (2013.01); *G01N 21/77* (2013.01); *G01N 33/521* (2013.01)

(58) Field of Classification Search
None
See application file for complete search history.

(56) References Cited

U.S. PATENT DOCUMENTS

| 4,553,848 | A | 11/1985 | Rosicke et al. |
| 5,463,467 | A | 10/1995 | Baumann et al. |
| 6,036,919 | A | 3/2000 | Thym et al. |
| 6,493,069 | B1 | 12/2002 | Nagashimada et al. |
| 7,132,270 | B2 | 11/2006 | Kratzsch et al. |
| 7,547,535 | B2 | 6/2009 | Kratzsch et al. |
| 7,630,084 | B2 | 12/2009 | Wehowski et al. |
| 2005/0023152 | A1 | 2/2005 | Surridge et al. |
| 2006/0003397 | A1 | 1/2006 | Knappe et al. |
| 2008/0213809 | A1 | 9/2008 | Heindl et al. |
| 2009/0208989 | A1 | 8/2009 | Petrich et al. |
| 2011/0143416 | A1 | 6/2011 | Horn et al. |
| 2011/0201909 | A1 | 8/2011 | Emery et al. |

FOREIGN PATENT DOCUMENTS

| EP | 0 821 234 A2 | 1/1998 |
| EP | 0 974 303 A1 | 1/2000 |
| EP | 1 359 409 A2 | 11/2003 |
| EP | 1 566 637 A1 | 8/2005 |
| EP | 1 780 288 A1 | 5/2007 |
| WO | WO 1993/012418 A2 | 6/1993 |
| WO | WO 2005/045016 A2 | 5/2005 |
| WO | WO 2007/012494 A1 | 2/2007 |
| WO | WO 2009/103540 A1 | 8/2009 |
| WO | WO 2013/112856 A2 | 8/2013 |

OTHER PUBLICATIONS

Freeman et al., "Biosensing and Probing of Intracellular Metabolic Pathways by NADH-Sensitive Quantum Dots", Angew Chem Int Ed 2009, vol. 48, pp. 309-313.*
Achatz, Daniela E. et al., "Luminescent Sensing of Oxygen Using a Quenchable Probe and Upconverting Nanoparticles", Angew. Chem. Int. Ed., 2011, 50, pp. 260-263, 4 pages.
Baik et al., "Cooperative Effect of Two Surface Amino Acid Mutations (Q252L and E170K) in Glucose Dehydrogenase . . . ", Applied and Environmental Microbiology, vol. 71: p. 3285-3293, (2005) 9 pages.
Hoenes, Joachim et al.: The Technology Behind Glucose Meters: Test Strips, Diabetes Technology & Therapeutics, vol. 10, Supplement 1, 2008, S-10 to S-26, 17 pages.
International Patent Application PCT/EP2014/075639 International Search Report dated Feb. 3, 2015, 4 pages.
International Patent Application PCT/EP2014/075639 Written Opinion dated Apr. 6, 2015. 7 pages.
International Patent Application PCT/EP2014/075639. International Preliminary Report on Patentability. dated Feb. 22, 2016, 16 pages.
Johnson, L.F. et al., "Infrared-to-Visible Conversion by Rare-Earth Ions in Crystals", J. Appl. Phys., vol. 43, No. 3, Mar. 1972, pp. 1125-1137. 13 pages.

(Continued)

*Primary Examiner* — Michelle F. Paguio Frising
(74) *Attorney, Agent, or Firm* — Woodard, Emhardt, Moriarty, McNett & Henry LLP

(57) ABSTRACT

The present invention relates to a detector matrix for detecting at least one analyte in a sample, preferably a sample of a body fluid, comprising at least one enzyme active in the presence of said at least one analyte and at least one indicator reagent changing at least one optical property dependent on the activity of said enzyme, wherein said detector matrix further comprises up-converting phosphor particles, preferably UV-emitting up-converting phosphor particles. The invention further relates to a test element and a test device for detecting at least one analyte in a sample comprising the detector matrix of the invention, as well as to a method for the manufacture of a detector matrix, a method for the manufacture of a test element, and to a method for detecting an analyte in a sample, comprising contacting a detector matrix according to the invention with a sample suspected to comprise said analyte.

12 Claims, 9 Drawing Sheets

(56) References Cited

OTHER PUBLICATIONS

Kale et al., "Enhancement of blue upconversion luminesence in hexagonal NaYF4:Yb,Tm by using K and Sc ions." J Nanopart Res 16: 1850. (2013) 12 pages.

Li et al., "Highly efficient lanthanide upconverting nanomaterials: Progresses and challenges." Nano Today 8, 643. (2013). 34 pages.

Mader, Heike et al., "Optical Ammonia Sensor Based on Upconverting Luminescent Nanoparticles." Anal. Chem. 2010, 82, 5002-5004. 3 pages.

MAF 13 13th Conference on Methods and Applications of Fluorescent Abstracts. Sep. 8, 2013. pp. 1-248, XP055112849, Genoa, Italy. Retrieved from the internet: http://www.maf13.org/img/MAF13-Abstract.pdf. [retrieved May 18, 2016]. 285 pages.

Qin et al., "Ultraviolet upconversion luminescence of Gd3+ from Ho3+ and Gd3+ codoped oxide ceramic induced by 532-nm CW laser excitation." Optics Communications 284: 3114. (2011). 4 pages.

Shen et al., "Lanthanide-doped upconverting luminescent nanoparticle platforms for optical imaging-guided drug delicery and therapy." Advanced Drug Delivery Reviews 66:744. (2013). 12 pages.

Sun et al., "pH sensor based on upconverting luminescent lanthanide nanorods." Chem Commun 33: 5000. (2009). 3 pages.

Vazquez-Figuera et al., "Development of a Thermostable Glucose Dehydrogenase by a Structure-Guided Consensus Concept." Chem BioChem 8:2295. (2007). 7 pages.

Wang, Guofeng et al., "Controlled synthesis and luminescence properties from cubic to hexagonal NaYF4:Ln3+ (Ln=Eu and Yb/Tm) microcrystals", Journal of Alloys and Compounds 475, 2009, pp. 452-455. 4 pages.

Wu, Shiwei et al., "Non-blinking and photostable upconverted luminescence from single lanthanide-doped nanocrystals." PNAS 106(27):01917. (2013) 5 pages.

Ali, Reham et al., "Upconverting nanoparticle based optical sensor for carbon dioxide", Sensors and Actuators B: Chemical: International Journal Devoted to Research and Development of Physical and Chemical Transducers, Elsevier S.A, CH. CH, vol. 150, No. 1, Sep. 21, 2010, pp. 126-131, XP027278879 ISSN: 0925-4005, 6 pages.

Corstjens, P.L.A.M. et al., "Infrared up-converting phosphors for bioassays". IEE Proceedings-Nanobiotechnology, vol. 152, No. 2, Jan. 1, 2005. p. 64, XP05512270, ISSN: 1478-1581. DOI: 10.1049/ip-nbt:20045014. 10 pages.

Huang, Lihua et al., "A Simple Optical Reader for Upconverting Phosphor Particles Captured on Lateral Flow Strip". IEEE Sensors Journal, IEEE Service Center, New York, NY, US, vol. 9, No. 10, Oct. 1, 2009, pp. 1185-1191, XP011272622, ISSN: 1530-437X, DOI: 10.1109/JSEN.2009.2027416. 7 pages.

Päkkilä, Henna et al., "Quantitative Multianalyte Microarray Immunoassay Utilizing Upconverting Phosphor Technology", Analytical Chemistry, vol. 84, No. 20, Oct. 16, 2012, pp. 8628-8634, XP055112265, ISSN: 0003-2700, DOI: 10.1021/ac301719p. 7 pages.

Corstjens, P.L.A.M et al., "Up-Converting Phosphor Technology-Based Lateral Flow Assay for Detection of Schistosoma Circulating Anodic Antigen in Serum", Journal of Clinical Microbiology, vol. 46, No. 1, Oct. 2007. pp. 171-176, XP 055112256, ISSN: 0095-1137, DOI: 10.1128/JCM.00877-07. 6 pages.

Peng, Jianhong et al., "A new biosensor for glucose determination in serum based on up-converting flouorescence resonance energy transfer", Biosensors and Bioelectronics, Elsevier BV, NL., vol. 28, No. 1, Jul. 22, 2011, pp. 414-420, XP028340807, ISSN: 0956-5663, DOI: 10.1016/J.BIOS.2011.07.057. 7 pages.

Riuttamäki, Terhi, "Upconverting Phosphor Technology: Exceptional Photoluminescent Properties Light Up Homogeneous Bioanalytical Assays". Sep. 30, 2011. Retrieved from the internet: http://www.doria.fi/bitstream/handle/10024/71980/AnnalesAI427Riuttamaki.pdfd?sequence=1. [retrieved May 18, 2016]. 93 pages.

Mokkapati, Vijaya K. et al., "Evaluation of UPlink-RSV Prototype Rapid Antigen Test for Detection of Respiratory Syncytial Virus Infection". Ann. N.Y. Acad. Sci. 1098: 476-485 (2007). 10 pages.

\* cited by examiner

COMPOSITION COMPRISING UP-CONVERTING PHOSPHORS FOR DETECTING AN ANALYTE

CROSS-REFERENCE TO RELATED APPLICATION

This application is a continuation of Application No. PCT/EP2014/075639, filed Nov. 27, 2013, which claims the benefit of European Application No. 14172572.1 filed Jun. 16, 2014, European Application No. 14158504.2 filed Mar. 10, 2014, and European Patent Application No. 13194585.9 filed Nov. 27, 2013, the entire disclosures of which are hereby incorporated by reference.

FIELD OF THE INVENTION

The present invention relates to a detector matrix for detecting at least one analyte in a sample, preferably a sample of a body fluid, comprising at least one enzyme active in the presence of said at least one analyte and at least one indicator reagent changing at least one optical property dependent on the activity of said enzyme, wherein said detector matrix further comprises up-converting phosphor particles, preferably UV-emitting up-converting phosphor particles. The present invention further relates to a test element and a test device for detecting at least one analyte in a sample comprising the detector matrix of the present invention, as well as to a method for the manufacture of a detector matrix, a method for the manufacture of a test element, and to a method for detecting an analyte in a sample, comprising contacting a detector matrix according to the present invention with a sample suspected to comprise said analyte.

RELATED ART

In photon up-conversion, higher-energy photons are generated by absorption of two or more photons by an appropriate composition, followed by emission of one, higher-energy, photon. The transition from the excited state back to the ground state (or to another lower-energy level) causes luminescence at wavelengths shorter than the excitation wavelength, which is also known as anti-Stokes photoluminescence. Specific compositions showing photon up-conversion already at relatively low energy densities are the so-called up-converting phosphors (UCPs), which are inorganic crystals consisting of a transparent host lattice doped with, typically, trivalent lanthanide ions or transition metals. UCPs have been used in solid state sensing layers for the detection of carbon dioxide (Ali et al. (2010), Sensors and Actuators B 150: 126), oxygen (Achatz et al. (2011), Angew Chem Int Ed 50: 260), ammonia (Mader and Wolfbeis (2010), Anal Chem 82: 5002), and pH (Sun et al. (2009), Chem Commun 33: 5000).

UV-emitting UCPs were first reported more than forty years ago (Johnson et al. (1972), LJ Appl Phys 43:1125) and in particular materials with the composition $NaYF_4:Yb^{3+}$, $Tm^{3+}$ were reported to produce UV emission in the range of 350 nm (Wang et al. (2009), J Alloys and Compounds 475(1-2): 452). UV luminescence of nanocrystals of the aforesaid compositions was further improved by substitution with $K^+$ and $Sc^{3+}$ (Kale et al. (2013), J Nanopart Res 15: 1850). The optimal excitation wavelength of UV-emitting UCPs based on $NaYF_4$ was found to be 980 nm, i.e. in the near infrared range; however, $YGdHoO_3$ ceramics were described as providing UV upconversion upon irradiation with light of a wavelength of 532 nm (Qin et al. (2011), Optics Communications 284: 3114).

To improve physico-chemical properties of UCPs, various kinds of coatings have been proposed, including, i.e. silica coatings (Corstj ens et al. (2005), IEE Proc. Nanobiotechnol. 152(2): 64), hydrophobic and amphiphilic coatings (Wu et al. (2013), PNAS 106(27): 10917), and $NaYF_4$, gold, or polyethylemneimine (PEI) coatings (Li et al. (2013), Nano Today 8, 643).

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods are known to the skilled person which make use of test elements comprising one or more test chemistries (also referred to as detector chemistries, test chemicals or detector chemicals), which, in presence of the analyte to be detected, are capable of performing one or more detectable detection reactions, such as optically detectable detection reactions. With regard to these test chemistries, reference may be made e.g. to J. Hoenes et al.: The Technology Behind Glucose Meters: Test Strips, Diabetes Technology & Therapeutics, Volume 10, Supplement 1, 2008, S-10 to S-26. Other types of test chemistries are possible and may be used for performing the present invention.

Typically, one or more optically detectable changes in the test chemistry are monitored, in order to derive the concentration of the at least one analyte to be detected from these changes. Examples of test fields, test chemistries and methods for monitoring one or more optically detectable changes in the test fields are disclosed in EP 0 821 234 A2. Thus, as an example, the relative remission of the test field may be optically detected as a function of time, up to a defined end point of the chemical detection reaction. From the change in relative remission, the concentration of the analyte may be derived. Similar measurements detecting the quantity of light reflected from the test field as a function of time, up to a defined end point of the detection reaction, are disclosed in EP 0 974 303 A1.

For detecting the at least one change of optical properties of the test field, various types of detectors are known in the art. Thus, various types of light sources for illuminating the test fields as well as various types of detectors are known. Besides single detectors such as photodiodes, various types of devices using detector arrays having a plurality of photosensitive devices are known. Thus, in US 2011/0201909 A1, an arrangement for measuring the concentration of an analyte contained in a sample of a body fluid is disclosed. The arrangement, inter alia, comprises a light source and a detector array. Similarly, EP 1 359 409 A2 discloses an apparatus for determining the concentration of an analyte in a physiological sample. The apparatus includes at least one light source and a detector array.

Further, when using detector arrays, methods are known in the art for detecting errors and artifacts in the images acquired by the detector arrays. Thus, US 2011/0201909 discloses a correction algorithm which, inter alia, is capable of correcting for imperfections present in the reaction spot observed by the detector array. Similarly, EP 1 359 409 A2 discloses means for determining whether a sufficient amount of sample is present on each of a plurality of different detector areas, wherein only light detected from those areas determined to have sufficient sample is used for determining the concentration of the analyte.

However, errors caused by reflection of illuminating light or by direct entry of illumination light into the detector are still a frequent cause of inaccurate measurement, since in a typical setup, the light used for illumination has the same wavelength as the light detected, such that reflections cannot be differentiated from light actually passing through the sample. This drawback creates an unwanted background signal that lowers the dynamic range of the signal. Usually, this problem is solved by complex optic modules where the irradiation of the chemistry layer is performed at a distinct angle relative to the detector, such that an amount as low as possible of the irradiation light is reflected onto the detector. Moreover, it has been proposed in the art to solve this problem by using modulated irradiation and/or detection cycles (e.g. U.S. Pat. No. 4,553,848, U.S. Pat. No. 5,463,467, and U.S. Pat. No. 7,630,084). However, these methods require complex optical and/or electronic assemblies and improved methods are still desirable.

Problem to be Solved

There is, thus, a need in the art to provide reliable means to determine the concentration of a soluble analyte in a sample, e.g. of a body fluid. In particular, there is a need to provide means and methods avoiding the drawbacks of the prior art as discussed in detail above.

SUMMARY OF THE INVENTION

This problem is solved by a detector matrix, a diagnostic test element, device and system as well as by a method for detecting an analyte with the features of the independent claims. Preferred embodiments, which might be realized in an isolated fashion or in any arbitrary combination are listed in the dependent claims.

Accordingly, the present invention relates to a detector matrix for detecting at least one analyte in a sample, preferably a sample of a body fluid, comprising (i) at least one enzyme active in the presence of said at least one analyte and (ii) at least one indicator reagent changing at least one optical property dependent on the activity of said enzyme, wherein said detector matrix further comprises (iii) up-converting phosphor particles.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

The term "matrix", as used herein, relates to a mixture comprising the compounds as specified herein. It is understood by the skilled person that the composition may comprise additional components, e.g., preferably, buffer components (e.g., of phosphate buffered saline, Tris buffer, citrate buffer, glycerine phosphate buffer, or Good's buffer) or other salts, detergents, or the like, including components as specified herein below. It will also be understood by the skilled person that the matrix of the present invention may be an inhomogeneous mixture, e.g. a dispersion or mixture.

Preferably, the matrix of the present invention is a dry composition. The term "dry composition" as used herein means that the composition is essentially free of a solvent or a mixture of solvents. Essentially free as used herein means that at least 85%, at least 90%, at least 92%, at least 95%, or at least 98% of the solvent or solvent mixture which was originally present in a solution of the composition has been removed from the composition. Accordingly, it is, preferably, envisaged that the solvent or solvent mixture is present in the dry composition of the invention in an amount of up to 15%, and preferably, up to 10%, up to 8%, up to 5%, or up to 2%. More preferably, a dry composition is a composition comprising water in an amount of up to 15%, and most preferably, up to 10%, up to 8%, up to 5%, or up to 2%. Methods for determining residual water are known to the skilled person; preferably, residual water in a composition according to the present invention is determined using a phosphorus pentoxide sensor according to the method as described in WO 1993/012418. The aforementioned percentage values and the other percentage values referred herein used in order to define amounts refer to percent by weight (w/w). Such a composition of the invention is, preferably, a solid composition under normal conditions, i.e., under room temperature and normal pressure.

The term "detector matrix", as used herein, refers to a matrix of compounds comprising at least one enzyme as specified herein, at least one indicator reagent as specified herein, and up-converting phosphor particles as specified herein. Various possibilities of designing a detector matrix are known in the art. In this regard, reference may be made to the above-mentioned prior art documents. Specifically, reference may be made to J. Hoenes et al.: The Technology Behind Glucose Meters: Test Strips, Diabetes Technology & Therapeutics, Volume 10, Supplement 1, 2008, S-10 to S-26. However, other types of detector matrices are possible. Preferably, the detector matrix of the present invention is adapted to change at least one optical property in the presence of the analyte. More preferably, the detector matrix performs at least one optically detectable detection reaction in the presence of the analyte. Even more preferably, the detection reaction is a redox reaction. Most preferably, the detection reaction produces redox equivalents and/or electrons as intermediates and/or products. Preferably, the optically detectable signal produced by the detection reaction is proportional to the amount and/or to the concentration of the analyte in the sample.

Preferably, the detector matrix detailed supra, in addition to the components detailed above, comprises at least one redox cofactor and an agent capable of eliciting a change in at least one optical property of the at least one indicator reagent in the presence of redox equivalents. Preferred compositions of the detector matrix are shown herein in the examples.

The term "enzyme", as used herein, relates to a macromolecule, preferably a polypeptide, having the catalytic properties as described herein. Preferably, the enzyme catalyzes the detection reaction of the present invention or a part thereof, i.e. at least a partial reaction, more preferably the rate-limiting partial reaction. Preferably, the enzyme catalyzes the detection reaction or a partial reaction thereof indirectly. More preferably, the enzyme catalyzes the detection reaction or a partial reaction thereof directly. Preferably, the enzyme interacts with the analyte. More preferably, the interaction is direct, i.e. the enzyme and the analyte are in direct physical contact in the course of the detection reaction. Most preferably, the analyte is a substrate of the enzyme. Thus, preferably, the at least one enzyme is preferably selected or adapted for performing at least one enzymatic reaction in the presence of the analyte. Preferably, the enzyme is specific for the analyte, more preferably, the enzyme is highly specific for the analyte. The term "specific for the analyte", as used herein, relates to the property of the enzyme of the present invention of having a Michaelis constant $K_m$ for the analyte at least twofold, more preferably at least fivefold, or, most preferably, at least tenfold lower than for other substrates from the same chemical class of molecules, in particular chemical compounds present in a sample according to the present invention. Accordingly, the term "highly specific", as used herein, relates to the property of the enzyme of the present invention having a Michaelis constant $K_m$ for the analyte at least 20-fold, more preferably at least 50-fold, or, most preferably, at least 100-fold lower than for other substrates from the same chemical class of molecules, in particular chemical compounds present in a sample according to the present invention.

Preferably, the enzyme is a dehydrogenase or comprises a dehydrogenase or oxidoreductase. The term "dehydrogenase" as used herein refers to an enzyme which is capable of catalyzing the oxidation or reduction of a substrate by transferring hydrides ($H^-$) in a one-step-mechanism or $H^+/e^-$ in a two-step mechanism as redox equivalents to or from its redox cofactor as referred to herein elsewhere. Preferably, a dehydrogenase is a polypeptide which is capable of catalyzing the oxidation of a substrate by transferring hydrides ($H^-$) as described above as redox equivalents to an acceptor molecule, preferably, to a redox cofactor as referred to herein elsewhere. Dehydrogenases envisaged by the present invention are, preferably, those which depend on a redox cofactor (or sometimes referred to as co-enzyme) such as pyrrolo quinoline quinone (PQQ), nicotinamide-adenine-dinucleotide (NAD) or a derivative thereof, or a flavine cofactor, such as flavin-adenine-dinucleotide (FAD) or flavine mononucleotide (FMN). Preferred dehydrogenases are, in particular, lactate dehydrogenase (EC number 1.1.1.27 or 1.1.1.28), glucose dehydrogenases (see below), alcohol dehydrogenase (EC number EC number 1.1.1.1 or 1.1.1.2), L-amino acid dehydrogenase (EC number 1.4.1.5), glycerin dehydrogenase (EC number 1.1.1.6), malate dehydrogenase (EC number 1.1.1.37), 3-hydroxybutyrate dehydrogenase (EC number 1.1.1.30), or sorbitol dehydrogenase (EC number 1.1.1.14).

The at least one enzyme may comprise glucose oxidase and/or glucose dehydrogenase. However, other types of enzymes and/or other types of detector matrix or active components of the detector matrix may be used. More preferably, the dehydrogenase is a glucose dehydrogenase. Most preferably, said glucose dehydrogenase is selected from the group consisting of: glucose dehydrogenase (EC number 1.1.1.47), quinoprotein glucose dehydrogenase (EC number 1.1.5.2), in particular, Pyrrolo quinoline quinone (PQQ)-dependent glucose dehydrogenase (EC number 1.1.5.2), glucose-6-phospate dehydrogenase (EC number 1.1.1.49), nicotinamide adenine dinucleotide (NAD)-dependent glucose dehydrogenase (EC number 1.1.1.119) and flavin adenine dinucleotide (FAD)-dependent glucose dehydrogenase (EC number 1.1.99.10) or enzymatically active mutants thereof.

Enzymatically active mutants of the aforementioned enzymes can be obtained by substituting, adding or deleting one or more amino acids from the amino acid sequences reported for the aforementioned wild type enzymes in the prior art as recited before. Preferred mutants are the mutants of the PQQ-dependent glucose dehydrogenase having an improved substrate specificity compared to their wild type counterparts as disclosed in U.S. Pat. No. 7,132,270 or U.S. Pat. No. 7,547,535. Further mutants are those disclosed in Baik et al (Baik 2005, Appl Environ Microbiol 71: 3285), Vasquez-Figuera et al. (Vasquez-Figuera 2007, Chem BioChem 8: 2295), and WO 2005/045016. Preferred in accordance with the present invention is a glucose dehydrogenase (E.C. 1.1.1.47) mutant disclosed in WO2009/103540A1 (p. 21) having a mutation at least at amino acid positions 96, 170 and/or 252, herewith incorporated by reference. Preferred mutations envisaged at theses amino acid positions are substitutions of Glu96Gly, Glu170Arg or Lys and/or Lys252Leu.

The term "indicator reagent", as used herein, preferably, relates to a compound changing at least one optical property dependent on, preferably proportional to, the activity of the enzyme of the present invention. Preferably, the indicator reagent is an optical indicator substance, which performs at least one optically detectable property change when at least one of the enzymes or when the enzyme comprised in the detector matrix reacts with the analyte. Thus, the at least one indicator reagent preferably comprises one or more dyes performing a change in an optical property indicative of the enzymatic reaction of the at least one enzyme and the analyte.

The term "optical property", as used herein, relates to a property which can be detected by an optical instrument. Specifically, the optical property may be or may comprise at least one property selected from the group consisting of: a reflection property, a transmission property, an emission property, a scattering property, a fluorescence property, a phosphorescence property, a diffraction property, and a polarization property. Preferably, an optical property as referred to herein refers to a property of the indicator reagent which can be optically detected such as light absorption, light emission, light remission, or properties associated therewith. It will be understood that such a change of at least one optical property as used herein encompasses the detection of the presence of a property which was not detectable before, the detection of the absence of a property which has been detected before, and the detection of quantitative changes of a property, i.e., the detection of the change of the signal strength which correlates to the extent of the change of the at least one optical property. Preferred optical properties envisaged by the present invention are color, fluorescence, luminescence, or refractometry. The optical properties which are to be changed by the analyte envisaged according to the present invention depend on the type of indicator reagent. Dependent on the desired optical property to be detected in the detector matrix, the skilled person is in a position to select without further ado a suitable indicator reagent, in particular among those referred to herein elsewhere. Methods of converting the optical property as defined above into a physical signal which can be read as a measurement value are well known in the art and are described, e.g., in EP 0 821 234, EP 0 974 303, and US 2005/0023152.

The optical property of the indicator reagent, according to the present invention, changes dependent on the activity of the enzyme of the present invention. Thus, preferably, the change of the optical property only occurs if the enzyme catalyzes the detection reaction. More preferably, the change of optical property is proportional to the number of catalytic cycles undergone by the enzyme present in the detector matrix. Thus, most preferably, the change of optical property is proportional to the number of analyte molecules converted by the enzyme.

Preferably, the optical property changing in the indicator reagent is measurable in the detector matrix comprising said indicator reagent. Thus, the at least one optical property may be any property of the detector matrix which changes in the presence of the analyte and which can be transferred into an optical signal of any kind. Preferably, the change of the optical property and/or the signal generatable therefrom are proportional to the concentration of the analyte in the sample. Additionally or alternatively, a predetermined or determinable relationship between the optical property, the change of the optical property and/or the signal generatable therefrom and the concentration of the analyte in the sample may exist which may be used for deriving the concentration from the signal.

Preferably, as described above, the optical property is a change in color and/or in color intensity of the detector matrix, i.e., preferably, a change in the absorption and/or emission spectrum of the detector matrix. Thus, in the change of the optical property the optical property preferably is selected from the group consisting of: a reflection property, preferably a reflectance and/or a remission; transmission property, preferably an absorption; a color; a luminescence, preferably a fluorescence. Also preferably, the optical property is the concentration of a reduced or an oxidized redox mediator as described above, i.e., preferably, the optical property is the redox state of said indicator reagent comprised in the test chemistry. Methods of converting the optical property as defined above into a physical signal which can be read as a measurement value are well known in the art as described above.

The term "redox cofactor" as used herein refers to a molecule which can serve as an acceptor for enzymatically transferred redox equivalents and, in particular, hydride (H—). Preferably, the redox cofactor is PQQ, NAD or FAD. It will be understood that the redox cofactor to be included in the composition of the present invention depends on the properties of the dehydrogenase to be envisaged. For example, PQQ is combined in a composition according to the present invention with a PQQ dependent glucose dehydrogenase, NAD is combined in a composition according to the present invention with a NAD dependent glucose dehydrogenase, and FAD is combined in a composition according to the present invention with a FAD dependent glucose dehydrogenase. A redox cofactor according to the present invention may also preferably be a derivative of PQQ, NAD or FAD. Preferred derivatives of NAD are those disclosed in WO 2007/012494 which is herewith incorporated by reference with respect to the disclosed NAD/NADH and/or NADP/NADPH derivatives. More preferably, the redox cofactor in accordance with the present invention is carbaNAD as disclosed in WO 2007/012494. It is understood by the skilled person that in case the UCP is an UV-UCP, preferably, the redox cofactor is the indicator reagent.

The term "redox equivalents" as used herein relates to the concept commonly used in redox chemistry well known to the skilled person. Preferably, the term relates to electrons which are transferred from a substrate of the dehydrogenase to the redox cofactor or electrons transferred to the indicator reagent from the redox cofactor.

The term "sample", as used herein, refers to a sample of a body fluid, to a sample of separated cells or to a sample from a tissue or an organ or to a sample of wash/rinse fluid obtained from an outer or inner body surface. Preferably, the sample is a sample from a body fluid. As used herein, the term "body fluid" relates to all bodily fluids of a subject known to comprise or suspected to comprise the analyte of the present invention, including blood, plasma, lacrimal fluid, urine, lymph, cerebrospinal fluid, bile, stool, sweat, and saliva. Preferably, the body fluid is blood, serum, or plasma. Samples of body fluids can be obtained by well known techniques including, e.g., venous or arterial puncture, epidermal puncture, and the like.

The term "analyte", as used herein, relates to a chemical compound present in a sample, preferably in a body fluid. Preferably, the analyte is a small molecule, i.e., preferably, the analyte is not a biological macromolecule, more preferably, the analyte is an organic molecule, most preferably an organic molecule capable of undergoing a redox reaction in the presence of the test chemistry according to the present invention. Preferably, the analyte is a molecule of the subject's metabolism. Also preferably, the analyte is a low molecular weight chemical compound, more preferably a chemical compound with a molecular mass of less than 1000 u (1000 Da; $1.66 \times 10^{-24}$ kg). More preferably, the analyte is selected from the list consisting of glucose, lactate, cholesterol, and triglycerides. Preferably, the analyte is blood glucose and the actual concentration to be determined is at least 10 mg/dL, at least 50 mg/dL, at least 60 mg/dL, at least 70 mg/dL, at least 80 mg/dL, at least 90 mg/dL, at least 100 mg/dL, at least 110 mg/dL, at least 120 mg/dL, at least 130 mg/dL, at least 140 mg/dL, or at least 150 mg/dL.

The term "detecting" relates to the quantification of the amount of analyte present in a sample, i.e. measuring the amount or concentration of said analyte, preferably semi-quantitatively or, more preferably, quantitatively. The detection of the amount of the analyte can be accomplished in a variety of ways known to the skilled person or detailed herein. In accordance with the present invention, detecting the amount of the analyte can be achieved by all known means for detecting the amount of said analyte in a sample, provided that they are adapted to specifically detect the analyte of the present invention and are compatible with the requirements of the present invention. The term "amount" as used herein encompasses the absolute amount of the analyte referred to herein, the relative amount or concentration of the analyte referred to herein as well as any value or parameter which correlates thereto. Such values or parameters comprise intensity signal values from all specific physical or chemical, preferably optical, properties obtained from the analyte referred to herein by measurements. It is to be understood that values correlating to the aforementioned amounts or parameters can also be obtained by all standard mathematical operations.

The term "up-converting phosphor particles", abbreviated "UCP", is known to the skilled person and relates to phosphor particles, specifically inorganic rare-earth doped crystals, having the property of absorbing at least two photons of a first wavelength (also referred to as a longer wavelength), followed by the emission of a single photon of a second wavelength being shorter than the first wavelength (the second wavelength also being referred to as a shorter wavelength).

It is understood by the skilled person that the terms "longer" and "shorter" are relative terms relating to the relative wavelength of the absorbed photons as compared to the emitted photon. Accordingly, the photons absorbed by the UCP have lower energy, while the emitted photon has higher energy. Structurally, the UCP preferably is an inorganic crystal composed of a transparent host lattice doped with certain trivalent lanthanide ions or transition metals. Preferred host lattices comprise trivalent rare earth ions ($Y^{3+}$, $La^{3+}$, $Gd^{3+}$, $Sc^{3+}$), alkaline earth ions ($Ca^{2+}$, $Sr^{2+}$, $Ba^{2+}$), or transition metals ($Zr^{4+}$, $Ti^{4+}$), more preferably as halides (e.g., $NaYF_4$, $YF_3$, $LaF_3$), oxides (e.g., $Y_2O_3$, $ZrO_2$), or, most preferably, as oxysulfides (e.g., $Y_2O_2S$, $La_2O_2S$). Dopant ions, preferably, are selected from lanthanide ions and the transition metal ions $Ti^{2+}$, $Ni^{2+}$, $Mo^{3+}$, $Re^{4+}$ and $Os^{4+}$. More preferably, dopant ions are $Pr^{3+}$, $Nd^{3+}$, $Dy^{3+}$. Most preferably, dopant ions are $Er^{3+}$, $Tm^{3+}$, or $Ho^{3+}$. It is understood by the skilled person that the UCP may be co-doped, preferably with $Yb^{3+}$. Preferably, the amount of dopants depends on the type of dopant used. For $Er^{3+}$, the molar percentage is, preferably, 0.5% to 5%, more preferably 1% to 3%, most preferably 2%. For $Tm^{3+}$ or $Ho^{3+}$, the molar percentage is, preferably, 0.05% to 1%, more preferably 0.1% to 0.6%, most preferably 0.3%. $Yb^{3+}$ as a co-dopant is used at a molar percentage of preferably 1% to 50%, more preferably 5% to 30%, most preferably 18% to 25%. Preferably, the UCP comprises $Y_2O_3$:Yb, Er; more preferably the UCP consists of $Y_2O_3$:Yb, Er. Preferably, the UCPs are crystals of a size in the range of 5 nm to 400 μm. More preferably, the UCPs are nanocrystals with a size of less than 75 nm, most preferably 2 to 50 nm.

Preferably, the UCP is coated with one or more inert and/or hydrophilic coating(s), including surface modification with amphiphilic polymers, lipids, and silica shells, as reviewed in Shen et al. (2013), Adv Drug Delivery Rev 65:744. Preferred coatings are amorphous silica or, more preferably, polyacrylic acid. Alternatively or additionally, the surface of the UCP may be further functionalized, e.g. by tetraethyl orthosilicate condensation on the UCP particle, preferably under copolymerization of one or more organosilanes. In a preferred embodiment, particularly in case the UCP is an UV-UCP, the UCP is, preferably, coated with a hydrophobic coating, preferably by an encapsulation method known in the art. It is, however, also envisaged that the UCP is coated with a hydrophobic inner coating and a hydrophilic outer coating, preferably by encapsulation methods known to the skilled person.

Preferably, the UCP has at least one wavelength of maximal absorption $\lambda_1$ in the range of 700 nm or higher, more preferably 800 nm or higher, most preferably of 900 nm or higher. Preferably, at least one wavelength of maximal absorption of the UCP is in the range 700 nm to 1300 nm, more preferably in the range 800 to 1200 nm, or, most preferably, in the range 900 to 1100 nm. Preferably, the UCP has at least one wavelength of maximal emission $\lambda_2$ in the range 400 nm to 800 nm, more preferably in the range 500 nm to 700 nm, or, most preferably, in the range 550 to 660 nm. It is understood by the skilled person that for each UCP, $\lambda_1 > \lambda_2$. The skilled person understands that light emitted by the UCP is absorbed at least in part by the indicator reagent in the detector matrix. Thus, preferably, the absorption spectrum of the indicator reagent overlaps with the emission spectrum of the UCP. More preferably, the wavelength of maximal absorption of the indicator reagent lies within the range of wavelengths emitted by the UCP.

In a preferred embodiment, the UCP is an UV-emitting UCP (UV-UCP), i.e. an UCP having at least one emission maximum at a wavelength of less than 380 nm. More preferably, the UV-UCP is an UCP having at least one emission maximum at a wavelength in the range of 300 nm-375 nm, more preferably in the range of 340 nm-370 nm, most preferably in the range of 345 nm-365 nm. Preferably, the UV-UCP has at least one second emission maximum at a wavelength of visible and/or near-infrared light, more preferably at a wavelength corresponding to a wavelength of low absorption by the indicator reagent or the redox indicator, preferably corresponding to a wavelength of low absorption by the indicator reagent and the redox indicator, most preferably at 450 nm±10 nm and/or at 800 nm±20 nm. As used relating to the indicator reagent and the redox indicator, the term "wavelength of low absorption" relates to a wavelength at which an indicator reagent or a redox indicator has a relative absorption of less than 25%, preferably less than 10%, most preferably less than 5% of the absorption at the wavelength of its maximal absorption; preferably, the aforesaid wavelength of low absorption and wavelength of maximal absorption are determined by determining absorption of said indicator reagent or redox indicator in the range of 300 nm to 1000 nm, preferably in increments of at most 10 nm, more preferably in increments of at most 2 nm, most preferably in increments of at most 1 nm. Preferably, the UV-UCP is an UCP as described herein above comprising or more preferably, consisting of $NaYF_4$:$Yb^{3+}$, $Tm^{3+}$, preferably co-doped with $K^+$ and/or $Sc^{3+}$. More preferably, the UV-UCP is an UCP as described herein of the composition $Na_{1-x}K_xYF_4$:$Yb^{3+}$, $Tm^{3+}$ and/or $NaY_{1-x}Sc_xF_4$:$Yb^{3+}$, $Tm^{3+}$ as described in Kale et al., J Nanopart Res 15: 1850 (2013). Most preferably, the UV-UCP is an UCP as described herein of the composition $Na_{1-x}K_xYF_4$:$Yb^{3+}$, $Tm^{3+}$ with a content of $K^+$ of of 0 to 60 mol %, preferably 10 to 50 mol %, more preferably 20 mol %±10 mol %, most preferably 20 mol %±5 mol % and/or the UV-UCP is an UCP as described herein of the composition $NaY_{1-x}Sc_xF_4$:$Yb^{3+}$, $Tm^{3+}$ with a mol % content of Sc of 0 to 60 mol %, preferably 10 to 50 mol %, more preferably 20 mol %±10 mol %, most preferably 20 mol %±5 mol %. Preferably, the UV-UCP of the present invention has at least one wavelength of maximal absorption $\lambda_1$ in the range of 500 nm or higher, more preferably in the range of 700 nm or higher, still more preferably 800 nm or higher, most preferably of 900 nm or higher. Preferably, at least one wavelength of maximal absorption of the UCP is in the range 700 nm to 1300 nm, more preferably in the range 800 to 1200 nm, or, most preferably, in the range 900 to 1100 nm.

Advantageously, it was found in the work underlying the present invention that by using UCP in a detector matrix, background noise resulting from, e.g. light scattered on one of the layers of a test element or entering the detector directly from the light source, can be strongly reduced. Surprisingly, it was found that measurement by UCP illumination is possible even in the inhomogeneous mixture of a detector matrix according to the present invention and without the need for local enrichment of indicator reagent in the space surrounding the UCP. Moreover, an increase in signal yield was observed, providing for improved signal dynamics. Also, when using UV-UCP having an emission maximum in the range 350 nm to 360 nm, it was possible to directly detect reduction of NAD or cNAD by measuring decrease of UV emission detectable from the UV-UCP. This method was found to be particularly suitable if a second emission maximum of the UV-UCP at a wavelength of low absorption by NADH or cNADH was used for internal control measurements, e.g. by normalizing the signal measured at 365 nm with the signal intensity at a wavelength of 450 nm or of 800 nm. Moreover, it was found in the work underlying the present invention that excitation light of a wavelength of 700 nm or more, or in particular of 800 nm or more, is absorbed by blood constituents only to a small extent, making a measuring set-up possible which uses excitation irradiation from the side of the test strip contacted to a blood sample, and which detects emission on the opposite side; this solves the problem of reflected light interfering with measurement known from the usual same-side setups, in which light source and detector are arranged on the same side relative to the test strip. It will be understood by the skilled person that such a setup is, preferably, embodied in a single-layer test strip, reducing technical effort and cost of test strip production, as compared to conventional two-layer test strips.

The definitions made above apply mutatis mutandis to the following. Additional definitions and explanations made further below also apply for all embodiments described in this specification mutatis mutandis.

The present invention further relates to a detector matrix according to the present invention for use as a diagnostic. The present invention also relates to a detector matrix according to the present invention for use in the diagnosis of diabetes.

The term "diagnostic", as used herein, refers to any means for assessing the probability according to which a subject is suffering or will suffer from a disease or condition referred to in this specification. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population. Preferably, the diagnostic is a means for determining at least one emergency parameter and/or clinically relevant parameter, including, without limitation, lactate, ketones, liver parameters (e.g. transaminases like ALT and/or AST), creatinine, triglycerides, cholesterol, HDL, and the like; more preferably, the diagnostic is a means for determining blood glucose. Accordingly, preferably, the diagnostic is a means for diagnosing clinically relevant deviations from normal metabolism; more preferably, the diagnostic is a means for diagnosing diabetes.

The term "diabetes" or "diabetes mellitus", as used herein, refers to disease conditions in which the glucose metabolism is impaired. Said impairment results in hyperglycaemia. According to the World Health Organization (WHO), diabetes can be subdivided into four classes. Type 1 diabetes is caused by a lack of insulin. Insulin is produced by the so called pancreatic islet cells. Said cells may be destroyed by an autoimmune reaction in Type 1 diabetes (Type 1a). Moreover, Type 1 diabetes also encompasses an idio-pathic variant (Type 1b). Type 2 diabetes is caused by an insulin resistance. Type 3 diabetes, according to the current classification, comprises all other specific types of diabetes mellitus. For example, the beta cells may have genetic defects affecting insulin production, insulin resistance may be caused genetically or the pancreas as such may be destroyed or impaired. Moreover, hormone deregulation or drugs may also cause Type 3 diabetes. Type 4 diabetes may occur during pregnancy. Preferably, diabetes as used herein refers to diabetes Type 2. According to the German Society for Diabetes, diabetes is diagnosed either by a plasma glucose level being higher than 110 mg/dl in the fasting state or being higher than 220 mg/dl postprandial. Further preferred diagnostic techniques are well known in the art and are described in the standard text books of medicine, such as Stedman or Pschyrembl.

Further, the present invention relates to a test element for detecting at least one analyte in a sample comprising the detector matrix of the present invention.

The term "test element", as used herein, relates to a unit comprising the elements as described herein below, i.e., the test element comprises at least one detector matrix and, preferably, at least one carrier element. More preferably, the test element further comprises a test field comprising the detector matrix as detailed herein below. The test element may further optionally comprise at least one puncture element. Preferably, the test element is an optical test element. Preferably, the test element is a test strip, a test tape, or a test disc. Also preferably, the test element is a diagnostic test element. The carrier element preferably may be or may comprise a strip-shaped carrier element or a band-shaped carrier element. The carrier element, as an example, may be or may comprise one or more carrier materials, such as at least one carrier material selected from the group consisting of: a paper; a plastic, specifically a plastic foil; a metal, preferably a metal foil; a ceramic material; a laminate comprising two or more layers. The detector matrix may be applied to the carrier element in a direct or indirect fashion.

The test field of the test element of the invention comprises, preferably, a transparent foil onto which one, more preferably more than one film layer are applied. The film layers of the test element according to the invention are produced from dispersions or emulsions of polymeric film formers. Dispersion film formers contain microscopic polymer particles which are insoluble in the carrier liquid (usually water) and are finely dispersed in the carrier liquid. If the liquid is removed by evaporation during film formation, then the particles come closer and finely touch one another. The large forces which typically occur in this process and the gain in surface energy which accompanies the film formation results in the particles growing into a substantially closed film layer. Alternatively, it is also possible to use an emulsion of the film former in which this is dissolved in a solvent. The dissolved polymer is emulsified in a carrier liquid which is immiscible with the solvent. Polyvinyl esters, polyvinyl acetates, polyacrylic esters, polymethacrylic acid, polyacrylamides, polyamides and polystyrene are particularly suitable as polymers for such film formers. In addition to homopolymers, mixed polymerizates are also suitable such as of butadiene, styrene or maleic acid ester.

By adding a swelling agent that swells well (i.e., a substance which increases its volume when it takes up water), one does not only obtain layers which can be penetrated relatively rapidly by sample liquid but have good cell, e.g., erythrocyte and additionally also blood pigment, separation properties despite this opening effect of the swelling agent. The swelling properties should be so good that for a test in which the change of the at least one optical property is mainly dependent on the penetration of the sample liquid through the layer, the change of the measurable property is measurable after a maximum of one minute. Especially suitable swelling agents have proven to be methyl vinyl ether maleic acid anhydride copolymer, xanthan gum and methyl vinyl ether maleic acid copolymer.

Single layer layouts of test elements are known from the prior art, see, e.g., EP 1 566 637 and EP 1 780 288. More preferred two-layer layouts, preferably, comprise a first and a second film layer resting on top of one another in this order. It is important that the first layer located on the transparent foil scatters light considerably less than the overlying second layer. The non-coated side of the transparent foil is referred to as the detection side and the side of the second layer which is opposite to the side with which the second layer rests on the first layer is referred to as the sample application side. The two so-called film layers are located on a transparent foil in the test field of the diagnostic test carrier according to the invention. For this, those plastic foils come into consideration which are impermeable to liquid. Polycarbonate foil has proven to be particularly suitable. The two film layers can be produced from coating compounds which contain the same polymeric film formers or they can be produced from coating compounds which contain different polymeric film formers. Whereas the first layer contains a swelling agent and optionally a weakly light scattering filler, the second layer requires a swelling agent and in any case at least one pigment that scatters light strongly. In addition, the second layer can also contain non-porous fillers as well as porous fillers. As will be understood by the skilled person, in a preferred embodiment of a two- or more-layer test element according to the present invention, the UCPs may also be comprised in a layer being in spatial proximity, preferably adjacent, to a layer comprising components of an analyte detector matrix as specified elsewhere herein, preferably to the layer comprising the indicator reagent. Preferably, the analyte detector matrix is the first layer, i.e. preferably, the UCPs are comprised in a second and/or further layer. It is, however, also envisaged that the UCPs are comprised in the first layer and that the components of the detector chemistry are comprised in a second and/or further, preferably third, layer. Also preferably, the UCPs may also be comprised in a layer comprising components of the detector matrix, preferably the layer comprising the indicator reagent, and at least one further layer.

In a preferred embodiment, the test element of the present invention is adapted for a measurement setup in which excitation irradiation is supplied from the sample application side of the test element, and wherein detection of emission is performed on the opposite side of the test element ("through-sample measurement"). As will be appreciated by the skilled person, the term "sample application side" relates to the side of the plane formed by the carrier element of the test element to which the detector matrix was applied and which is contacted by the sample. It will be understood by the skilled person that in such case, preferably, at least one of the layers of the test element comprising the UCPs comprises a pigment that scatters light strongly. More preferably, in a test element adapted for through-sample measurement, a layer not comprising the indicator reagent, more preferably a layer comprising the UCPs, comprises a pigment that scatters light strongly. In a most preferred embodiment, a test element adapted for through-sample measurement is a single-layer test element wherein, preferably, the single layer comprises or consists of a detector matrix according to the present invention.

In the case of a single-layer film, the detector matrix of the present invention is comprised in said single layer. In the case of multi-layer (i.e., more than one layer) layouts, it is possible that the detector matrix of the invention is comprised in one film layer, preferably, the first film layer. However, it is also possible that the detector matrix of the present invention is present in two or more film layers.

In order to optimize the test field in the test element according to the invention, it has proven to be particularly advantageous when all film layers, preferably both layers in the case of two-layer layouts, do contain a non-haemolyzing wetting agent. Neutral, i.e., non-charged wetting agents are particularly preferred for this. N-octanoyl-N-methyl glucamide is most particularly preferred.

In order to produce a two-layer test field of a test element according to the invention, the respective film layers are each produced successively from a homogeneous dispersion of the said components. For this, the transparent foil is used as a base to form the coating compound for the first film layer. After the coating compound for the first film layer has been applied with a particular layer thickness, the layer is dried. Afterwards, the coating compound for the second layer is applied to this layer also with a thin layer thickness and dried. The test field produced in this manner can be mounted on a supporting layer for better handling, those materials coming into consideration for such a layer which do not take up the liquid to be examined. These are so-called non-absorptive materials, plastic foils for example made of polystyrene, polyvinyl chloride, polyester, polycarbonate or polyamide being particularly preferred. Metal foils or glass are suitable as further supporting materials.

In a preferred embodiment of the test element according to the invention, the detection side of the test field, which is to be observed and measured for a change in at least one optical property of the indicator reagent, is visible through the supporting layer in order to determine the analyte to be detected in the sample. This can be achieved by a transparent supporting layer. However, it is also possible that the supporting layer has a perforation which is covered by the detection side of the test field. The detection side is then visible through the perforation. Preferably, in the diagnostic test element according to the invention there is a hole in the supporting layer below the detection side of the test field through which the detection side of the test field can be observed. The hole has a somewhat smaller diameter than the smallest linear dimension of the test field so that the test field outside the hole rests on the supporting layer and can be attached there.

The present invention further relates to a test device comprising at least one receptacle for the diagnostic test element of the present invention and a detector comprising at least one light source adapted for illuminating the diagnostic test element with light having a first wavelength $\lambda_1$, and at least one optically sensitive element adapted for detecting light having a second wavelength $\lambda_2$, emitted by the diagnostic test element, the second wavelength being a lower wavelength as compared to the first wavelength. The test device may be handled in an isolated fashion, without the test element. Alternatively, the test device itself may comprise one, two or more test elements according to the present invention.

The term "test device" as used herein, relates to a test device in principle known in the art, however, adapted to measure the analyte-induced change of the optical property as specified herein above. Accordingly, the test device of the present invention comprises at least one receptacle for the test element of the present invention, at least one light source adapted for illuminating the test element with light having a first wavelength $\lambda_1$, and at least one detector adapted for detecting light having a second wavelength $\lambda_2$, emitted by the test element. According to the present invention, the second wavelength is a lower wavelength as compared to the first wavelength, i.e. $\lambda_1 > \lambda_2$, and the test device is adapted accordingly. Preferably, the wavelengths in the context of the test device of the present invention are the same as detailed herein above for the UCP, meaning that, preferably, the test device is adapted to illuminate the test element with light of the wavelength of maximal absorption of the UCP used; similarly, preferably, the test device is adapted to detect light of the wavelength of maximal emission of the UCP. However, it is also envisaged that for illumination and/or detection of emission, wavelengths deviating up to 50 nm from the above-mentioned wavelengths are used, e.g. in order to avoid interference by other compounds at the optimal wavelength. Preferably, the test device is a diagnostic test device. Preferably, the test device further comprises at least one sensor for determining an ambient parameter. More preferably, the test device further comprises at least one temperature sensor for determining an ambient temperature. Also preferably, the test device is a hand-held test device.

In a preferred embodiment, the test device according to the present invention is adapted for through-sample measurement. Thus, preferably, in the test device, preferably, the light source is arranged such that it illuminates the test element from the sample application side, and the detector is arranged on the opposite side relative to the test element, i.e., preferably, the side of the test element terminating with the transparent carrier foil.

The term "test element receptacle" is known to the skilled person and relates to an element of the test device shaped for receiving at least one test element according to the present invention, providing one or more connectors and/or detectors as appropriate for detecting an analyte in a body fluid, and, preferably, adapted to locate the test element in at least one application position in which a sample of the body fluid is applicable to the test element. The specific embodiment of the test element receptacle, preferably, will depend on the kind of test element and on the test chemistry used therein. Thus, as an example, the test element receptacle may be or may comprise one or more of: a slot for fully or partially inserting the at least one test element, preferably a strip-shaped test element; an open space within a housing to fully or partially receive the at least one test element; a magazine for receiving one or more test elements; a guiding for holding and/or moving one or more of the test elements.

The term "detector" is generally known to the skilled person. Thus, the detector may be or may comprise at least one device for measuring at least one property of the detector matrix, such as the at least one optical property, and/or of a change thereof. As an example, the detector may be or may comprise at least one light-sensitive device, such as a photo-cell, a photo-diode, a solar cell, a multiplier tube or any arbitrary combination thereof. The detector may be adapted to transform at least one light signal into at least one analogue and/or digital electrical signal. The detector of the present invention comprises at least one light source and an optically sensitive element, both as defined herein below.

The term "light source" is understood by the skilled person and relates to any means for illuminating a test element and/or a test field comprised therein at an appropriate wavelength, e.g., preferably, a laser or laser diode and/or a light emitting diode (LED), more preferably an LED operated in pulse mode. The light source according to the present invention is adapted for illuminating the diagnostic test element with light having a first wavelength $\lambda_1$ as specified herein above. Preferably, the light source according to the present invention is adapted for illuminating the diagnostic test element with light essentially consisting of photons of a first wavelength $\lambda_1$ as specified herein above. The term "essentially consisting of", as used herein in the context of a wavelength, relates to light comprising less than 50% of photons having a wavelength deviating more than 10% from the given wavelength. Mutatis mutandis, the term "essentially detecting" relates to a detection mode wherein more than 50% of the photons detected have a wavelength deviating less than 10% from the given wavelength.

Preferably, the light source comprises a photon generating device, more preferably a photon generating device emitting light essentially consisting of photons of a defined wavelength, most preferably $\lambda_1$ as specified herein above. Also preferably, the light source further comprises at least one filter unit intervening the photon generating device and the test element, wherein the filter unit causes only light essentially consisting of photons of a defined wavelength, most preferably $\lambda_1$ as specified herein above, to irradiate the diagnostic test element.

The term "optically sensitive element" is known to the skilled person and relates to any means of detecting photons, preferably of a wavelength as specified herein, such as one or more of: a photo cell, a photo diode, a solar cell, a photo transistor, a photosensitive semiconductor device, a CCD or CMOS chip. The skilled person, as described above, knows how to use different test chemistries and how to use an appropriate detector for the respective detector matrix. Thus, preferably, the detector is adapted to measure the optical property of the detector matrix as described herein above. Preferably, the detector comprises a one-dimensional or two-dimensional matrix of optically sensitive elements, e.g., preferably, a camera chip, more preferably a CCD chip. According to the present invention, the optically sensitive element is adapted for detecting light comprising photons of a second wavelength $\lambda_2$, as defined herein above, emitted by the diagnostic test element. Accordingly, the detector comprises at least one optically sensitive element to detect light emitted by a test field. Said optically sensitive element may, e.g., be a photo diode. Preferably, the optically sensitive element essentially detects light consisting of photons of a defined wavelength, most preferably $\lambda_2$ as specified herein above. Preferably, the detector comprises a filter unit intervening the diagnostic test element and the optically sensitive element. More preferably, the filter unit causes only light essentially consisting of photons of said wavelength $\lambda_2$ emitted by the diagnostic test element to be detected by said optically sensitive element.

Advantageously, it was found in the work underlying the present invention, that by using a UCP-comprising detector matrix, the test device can be simplified as compared to the prior art: by including a high-pass filter between the test element and the sensor, or by using a sensor insensitive to excitation light having a longer wavelength, problems related to reflection of excitation light can be avoided in a simple manner.

Further, the present invention relates to a test system, preferably a diagnostic test system, comprising the test device of the present invention and further comprising the test element of the present invention.

The present invention further relates to various methods, as will be disclosed in further detail below. The methods include the method steps as described below. In case a plurality of method steps are comprised within one method, the method steps may be performed in the given order or in a different order. The method may further comprise one or more additional method steps which are not listed. Further, the method steps may be performed such that two or more method steps are performed simultaneously or in a timely overlapping fashion. Further, one, two or more or even all of the method steps may be performed once or repeatedly.

Thus, in a further aspect of the present invention, the present invention relates to a method for the manufacture of a detector matrix comprising mixing the components according to the present invention.

Also, the present invention relates to a method for the manufacture of a test element comprising the step of generating a detector matrix of the present invention on a carrier.

Further, the present invention relates to a method for detecting at least one analyte in a sample, comprising the steps of: (a) contacting a diagnostic test element according to the present invention with a sample suspected to comprise said at least one analyte; (b) measuring a change in at least one optical property of the indicator reagent comprised in the detector matrix of the diagnostic test element, whereby (c) the presence or amount of the analyte in the body fluid sample is determined.

The method for detecting at least one analyte of the present invention, preferably, is an in vitro method. Moreover, the methods of the present invention may comprise steps in addition to those explicitly mentioned above. For example, in the method for detecting at least one analyte, further steps may relate, e.g., to obtaining a sample for step a), or performing calculations on the measured change in step b) in order to obtain, e.g., the value of the concentration of the analyte in the sample. Moreover, one or more of said steps may be performed by automated equipment.

Preferably, measuring a change in at least one optical property of the indicator reagent comprises irradiating the diagnostic test element with light comprising photons having a first wavelength $\lambda_1$ and detecting photons emitted from the diagnostic test element having a second wavelength $\lambda_2$, wherein $\lambda_1 > \lambda_2$. More preferably, measuring a change in at least one optical property of the indicator reagent comprises irradiating the diagnostic test element with light essentially consisting of photons having a first wavelength $\lambda_1$ and detecting photons emitted from the diagnostic test element having a second wavelength $\lambda_2$, wherein $\lambda_1 > \lambda_2$. Even more preferably, measuring a change in at least one optical property of the indicator reagent comprises irradiating the diagnostic test element with light comprising photons having a first wavelength $\lambda_1$ and essentially detecting photons emitted from the diagnostic test element having a second wavelength $\lambda_2$, wherein $\lambda_1 > \lambda_2$. Most preferably, measuring a change in at least one optical property of the indicator reagent comprises irradiating the diagnostic test element with light essentially consisting of photons having a first wavelength $\lambda_1$ and essentially detecting photons emitted from the diagnostic test element having a second wavelength $\lambda_2$, wherein $\lambda_1 > \lambda_2$.

In a preferred embodiment, a change in at least one optical property is normalized to a signal obtainable from a second emission maximum of the up-converting phosphor particle and, accordingly, measuring a change in at least one optical property of the indicator reagent further comprises detecting photons emitted from the diagnostic test element having a third wavelength $\lambda_3$ and normalizing the number of photons detected at said second wavelength $\lambda_2$ to the number of photons detected at said third wavelength $\lambda_3$, wherein said third wavelength $\lambda_3$ is a wavelength of a second emission maximum of the UV-emitting up-converting phosphor particle present in said detector matrix or in said detector matrix of said test element, wherein $\lambda_1 > \lambda_3$.

In a preferred embodiment, measuring a change in at least one optical property of the indicator reagent comprised in the detector matrix of the diagnostic test element, i.e. step (b) of the method for detecting at least one analyte in a sample, comprises irradiating said diagnostic test element from the sample application side and detecting emission on the side opposite to said sample application side.

Further, the present invention relates to a use of an up-converting phosphor particle for the manufacture of a detector matrix according to the present invention or of a diagnostic test element according to the present invention.

Also, the present invention relates to a use of the detector matrix according to the present invention for the manufacture of a diagnostic.

Moreover, the present invention relates to a use of the detector matrix according to the present invention for the manufacture of a diagnostic for the diagnosis of diabetes.

Moreover, the present invention relates to a covering layer matrix, comprising a polymeric film former and up-converting phosphor particles.

As used herein, the term "covering layer matrix" relates to a matrix as specified herein above, comprising at least a polymeric film former and UCPs. Preferably, the covering layer matrix is a matrix adapted for use in close proximity to an analyte detector matrix. As will be understood by the skilled person, the analyte detector matrix, preferably, is any detector matrix known from the art or the analyte detector matrix is a detector matrix according to the present invention. More preferably, the covering layer matrix is a matrix adapted for physically contacting an analyte detector matrix. Still more preferably, the covering layer matrix is a matrix adapted for forming a further layer on a two- or more-layer test element, most preferably the second layer, i.e. preferably, upper, layer of a two-layer test element.

The term "polymeric film former" or "dispersion film former" is known in principle to the skilled person and is further specified herein above. Preferably, the polymeric film former is or comprises polymer particles insoluble in the carrier liquid (usually water), said polymer particles being, preferably, dispersed in suspension in the liquid carrier. More preferably, the polymeric film former is selected from the group consisting of polyvinyl esters, polyvinyl acetates, polyacryl esters, polymethacrylic acids, polyvinylamides, polyamides and polystyrene. In addition to homopolymers, also copolymers, preferably those of butadiene, styrene or of maleic acid esters are suitable. Also preferred film formers are those disclosed herein in the examples.

Preferably, the covering layer matrix further comprises a filling agent. Filling agents are known in the art and include $SiO_2$, silicates, and aluminium-silicates. Preferably, the filling agent is an aluminium-silicate with a composition of 66% (w/w) $SiO_2$, 26% (w/w) $Al_2O_3$, 7% (w/w) $Na_2O$, and 1% (w/w) $SO_3$, which is, e.g., preferably, sold under the trademark TRANSPAFILL™; a silicate with a $SiO_2$ content of ≥97% and a particle size (d50) of 7.5, which is sold, e.g., preferably, sold under the trademark SIPERNAT® 320 DS; or a hydrophilic pyrogenic mixed oxide sold, preferably, under the trademark AEROSIL®, more preferably, AERO- SIL® COK84. Also preferred filling agents are those disclosed herein in the examples.

The covering layer matrix of the present invention, preferably, comprises further components as described elsewhere herein above. As will be understood, the further components potentially comprised in the covering layer matrix of the present invention will depend on the application for which the covering layer matrix is intended.

As specified elsewhere herein, it is a preferred embodiment of the present invention that the covering layer matrix is adapted for use as a reflecting layer in a two- or more-layer test element. In such case, the covering layer matrix, preferably, further comprises a strongly light-scattering agent. Strongly light-scattering agents are, in principle, known in the art and include, preferably, agents having a refractive index of at least 2, more preferably at least 2.5. The skilled person knows how to determine the refractive index of a chemical compound. If not otherwise noted, the refractive index according to the present invention is the refractive index of the solid compound determined at 589 nm. More preferably, the strongly light-scattering agent is a metal oxide, including mixed transition metal oxides. Still more preferably, the strongly light-scattering agent is $TiO_2$, preferably with an average particle diameter of 0.2 µm to 0.8 µm. The average particle diameter, preferably, is determined using a Laser-granulometer, Type 715, manufactured by the company Pabisch, Munich, Federal Republic of Germany, preferably according to manufacturer's instructions. In also preferred embodiments, the strongly light-scattering agent is $ZrO_2$, $BaSO_4$, $HfO_2$, or $Y_2O_3$.

In another preferred embodiment, the covering layer matrix of the present invention is adapted for use as an illumination layer, i.e. as a layer adjacent, more preferably immediately adjacent, to an analyte detector matrix. More preferably, said covering layer matrix adapted for use as an illumination layer is further adapted for use as the second layer of a two- or more-layer test element as specified herein above. In such case, the covering layer matrix, preferably, does not comprise a strongly light-scattering agent. More preferably, said covering layer matrix does not comprise an agent having a refractive index of greater or equal to 2, more preferably of greater or equal to 1.5. As will be appreciated by the skilled person, a covering layer matrix adapted for use as an illumination layer is particularly suited for use in a through-sample measurement as specified herein above.

The invention further discloses and proposes a computer program including computer-executable instructions for performing the method according to the present invention in one or more of the embodiments enclosed herein when the program is executed on a computer or computer network. Specifically, the computer program may be stored on a computer-readable data carrier. Thus, specifically, one, more than one or even all of method steps a) to d) as indicated above may be performed by using a computer or a computer network, preferably by using a computer program. Preferably, at least method step (c) or at least method steps (b) and (c) are performed by using a computer or a computer program.

The invention further discloses and proposes a computer program product having program code means, in order to perform the method according to the present invention in one or more of the embodiments enclosed herein when the program is executed on a computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute the method according to one or more of the embodiments disclosed herein.

The invention further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing the method according to one or more of the embodiments disclosed herein.

Preferably, referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present invention further discloses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

All references cited in this specification are herewith incorporated by reference with respect to their entire disclosure content and the disclosure content specifically mentioned in this specification.

Summarizing the findings of the present invention, the following embodiments are preferred:

Embodiment 1

A detector matrix for detecting at least one analyte in a sample, preferably a sample of a body fluid, comprising (i) at least one enzyme active in the presence of said at least one analyte and (ii) at least one indicator reagent changing at least one optical property dependent on the activity of said enzyme, wherein said detector matrix further comprises (iii) up-converting phosphor particles.

Embodiment 2

The detector matrix of embodiment 1, wherein the optical property is a property selected from the group consisting of light absorption, light emission, or light remission.

Embodiment 3

The detector matrix of embodiment 1 or 2, wherein the detector matrix further comprises (iv) at least one redox cofactor and (v) an agent capable of eliciting a change in at least one optical property of said at least one indicator reagent in the presence of redox equivalents, and wherein the enzyme is a dehydrogenase.

Embodiment 4

The detector matrix of embodiment 3, wherein the dehydrogenase is a glucose dehydrogenase.

Embodiment 5

The detector matrix of any one of embodiments 1 to 4, wherein the up-converting phosphor particles are coated with at least one of an inert coating matrix and a hydrophilic coating matrix.

Embodiment 6

The detector matrix of any one of embodiments 1 to 5, wherein the up-converting phosphor particles comprise and preferably consist of $Y_2O_2S:Yb, Er$.

Embodiment 7

The detector matrix of any one of embodiments 1 to 5, wherein the up-converting phosphor particles are UV-emitting up-converting phosphor particles (UV-UCP).

Embodiment 8

The detector matrix of any one of embodiments 1 to 5 or 7, wherein the up-converting phosphor particles comprise, or preferably consist of, $NaYF_4:Yb^{3+}, Tm^{3+}$, preferably co-doped with $K^+$ and/or $Sc^{3+}$.

Embodiment 9

A detector matrix according to any one of embodiments 1 to 8 for use as a diagnostic.

Embodiment 10

A detector matrix according to any one of embodiments 1 to 8 for use in the diagnosis of diabetes.

Embodiment 11

A test element for detecting at least one analyte in a sample comprising the detector matrix of any one of embodiments 1 to 8 or comprising the components of the detector matrix of any one of embodiments 1 to 8.

Embodiment 12

The test element according to embodiment 11, further comprising at least one carrier element, wherein the detector matrix is applied to the carrier.

Embodiment 13

The test element according to embodiment 11 or 12, wherein the test element comprises at least one test field, wherein the test field comprises the detector matrix.

Embodiment 14

The test element of embodiment 13, wherein the test field comprises at least one detection layer comprising the detector matrix and at least one additional layer.

Embodiment 15

The test element according to any one of embodiments 11 to 14, wherein said test element is adapted for detecting said at least one analyte by irradiating said test element at the sample application side and by detecting emission at the side opposite to said sample application side.

Embodiment 16

A test device comprising at least one receptacle for the diagnostic test element according to any one of embodiments 11 to 15 and a detector comprising
(i) at least one light source adapted for illuminating the diagnostic test element with light having a first wavelength $\lambda_1$, and
(ii) at least one optically sensitive element adapted for detecting light having a second wavelength $\lambda_2$, emitted by the diagnostic test element, the second wavelength being a lower wavelength as compared to the first wavelength.

Embodiment 17

The test device of embodiment 16, wherein the light source comprises a photon generating device and, preferably, comprises a filter unit intervening the photon generating device and the diagnostic test element, wherein the photon generating device or the filter unit or the combination thereof causes only light essentially consisting of photons of said wavelength $\lambda_1$ to irradiate the diagnostic test element.

Embodiment 18

The test device of embodiment 16 or 17, wherein the detector comprises a photon detecting device and, preferably, comprises a filter unit intervening the diagnostic test element and the photon detecting device, wherein the photon detecting device or the filter unit or the combination thereof causes only light essentially consisting of photons of said wavelength $\lambda_2$ emitted by the diagnostic test element to be detected by said photon detecting device.

Embodiment 19

The test device of any one of embodiments 16 to 18, wherein at least one light source is adapted for illuminating the diagnostic test element from the sample application side and wherein at least one optically sensitive element is adapted for detecting light emitted by the diagnostic test element from the side opposite to said sample application side.

Embodiment 20

A test system, the test system comprising the test device of any one of embodiments 16 to 19 and further comprising the test element of any one of embodiments 11 to 15.

Embodiment 21

A method for the manufacture of a detector matrix comprising mixing the components according to any one of embodiments 1 to 9.

Embodiment 22

A method for the manufacture of a test element comprising the step of generating a detector matrix according to any one of embodiments 1 to 9 on a carrier.

Embodiment 23

A method for detecting at least one analyte in a sample, comprising the steps of:
(a) contacting a detector matrix according to any one of embodiments 1 to 10 with a sample suspected to comprise said at least one analyte;
(b) measuring a change in at least one optical property of the indicator reagent comprised in the detector matrix of the diagnostic test element, whereby
(c) the presence or amount of the analyte in the body fluid sample is determined.

Embodiment 24

The method according to embodiment 23, wherein measuring a change in at least one optical property of the indicator reagent comprises irradiating the diagnostic test element with light comprising photons having a first wavelength $\lambda_1$ and detecting photons emitted from the diagnostic test element having a second wavelength $\lambda_2$, wherein $\lambda_1 > \lambda_2$.

Embodiment 25

The method of embodiment 24, wherein measuring a change in at least one optical property of the indicator reagent further comprises detecting photons emitted from the diagnostic test element having a third wavelength $\lambda 3$ and normalizing the number of photons detected at said second wavelength $\lambda 2$ to the number of photons detected at said third wavelength $\lambda 3$, wherein said third wavelength $\lambda 3$ is a wavelength of a second emission maximum of the UV-emitting up-converting phosphor particle present in said detector matrix or in said detector matrix of said test element, wherein $\lambda_1 > \lambda_3$.

Embodiment 26

The method of embodiment 24 or 25, wherein $\lambda_1$ is 700 nm or higher, preferably, 850 nm or higher.

Embodiment 27

The method of embodiment 25 or 26, wherein $\lambda_3$ is 700 nm or higher, preferably 750 nm or higher.

Embodiment 28

Use of an up-converting phosphor particle for the manufacture of a detector matrix according to any one of embodiments 1 to 9 or of a diagnostic test element according to embodiment 11 to 15.

Embodiment 29

Use of the detector matrix according to embodiment 1 to 9 for the manufacture of a diagnostic.

Embodiment 30

Use of the detector matrix according to embodiment 1 to 9 for the manufacture of a diagnostic for the diagnosis of diabetes.

Embodiment 31

A covering layer matrix, comprising a polymeric film former and up-converting phosphor particles.

Embodiment 32

The covering layer matrix of embodiment 31, further comprising a filling agent, preferably $SiO_2$, a silicate, or an aluminum-silicate, more preferably an aluminum-silicate with a composition of 66% (w/w) $SiO_2$, 26% (w/w) $Al_2O_3$, 7% (w/w) $Na_2O$, and 1% (w/w) $SO_3$.

Embodiment 33

The covering layer matrix of embodiment 31 or 32, further comprising a strongly light-scattering agent.

Embodiment 34

The covering layer matrix of embodiment 33, wherein said strongly light-scattering agent is an agent having a refractive index of at least 2.

Embodiment 35

The covering layer matrix of embodiment 33 or 34, wherein said strongly light-scattering agent is $TiO_2$, preferably with an average particle diameter of 0.2 μm to 0.8 μm.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

Figure 3:
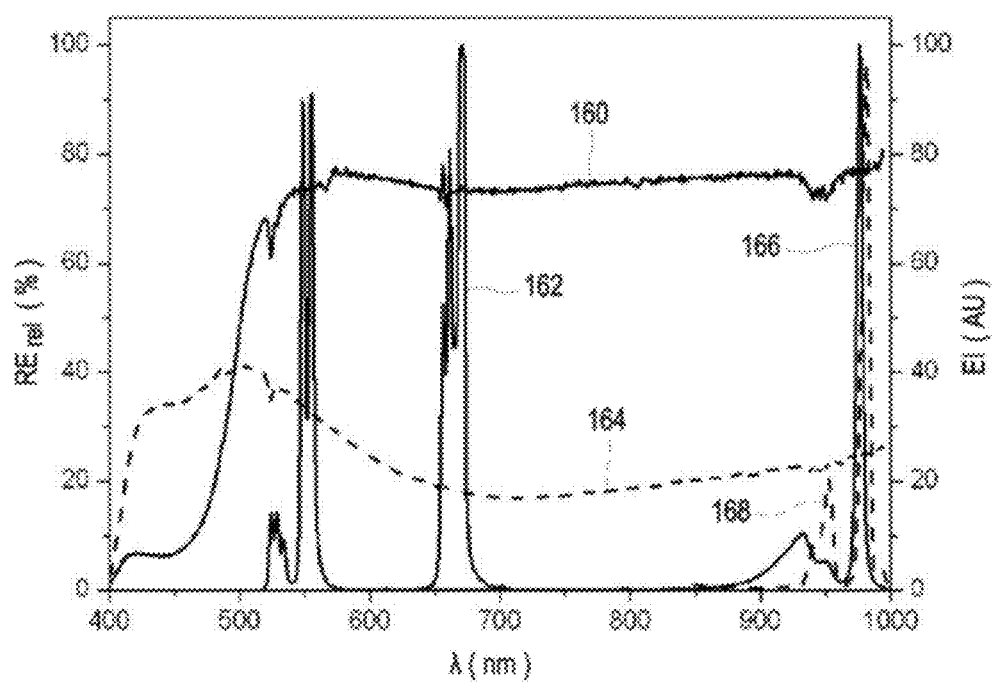

FIG. 3 shows spectra of the IR laser, of UCP excitation and emission and of the re-emission of a standard test strip according to the prior art comprising a PMo dye (Phosphor molybdic acid) in the presence and in the absence of glucose. 168: UCP excitation, from the documentation of the manufacturer (Honeywell Product Data Sheet 53101 Lumilux® Green UC2); 166: IR-laser spectrum; 162: UCP emission, measured from the test strip; 160: light reflected from a conventional teststrip in the presence of glucose; 164: light reflected from a conventional teststrip in the absence of glucose. Y-Axis: $RE_{rel}$: relative re-emission of the PMo dye (%) and EI: Laser and UCP emission intensity (arbitrary units, AU). X-Axis: $\lambda$: wavelength (nm).

Figure 4:
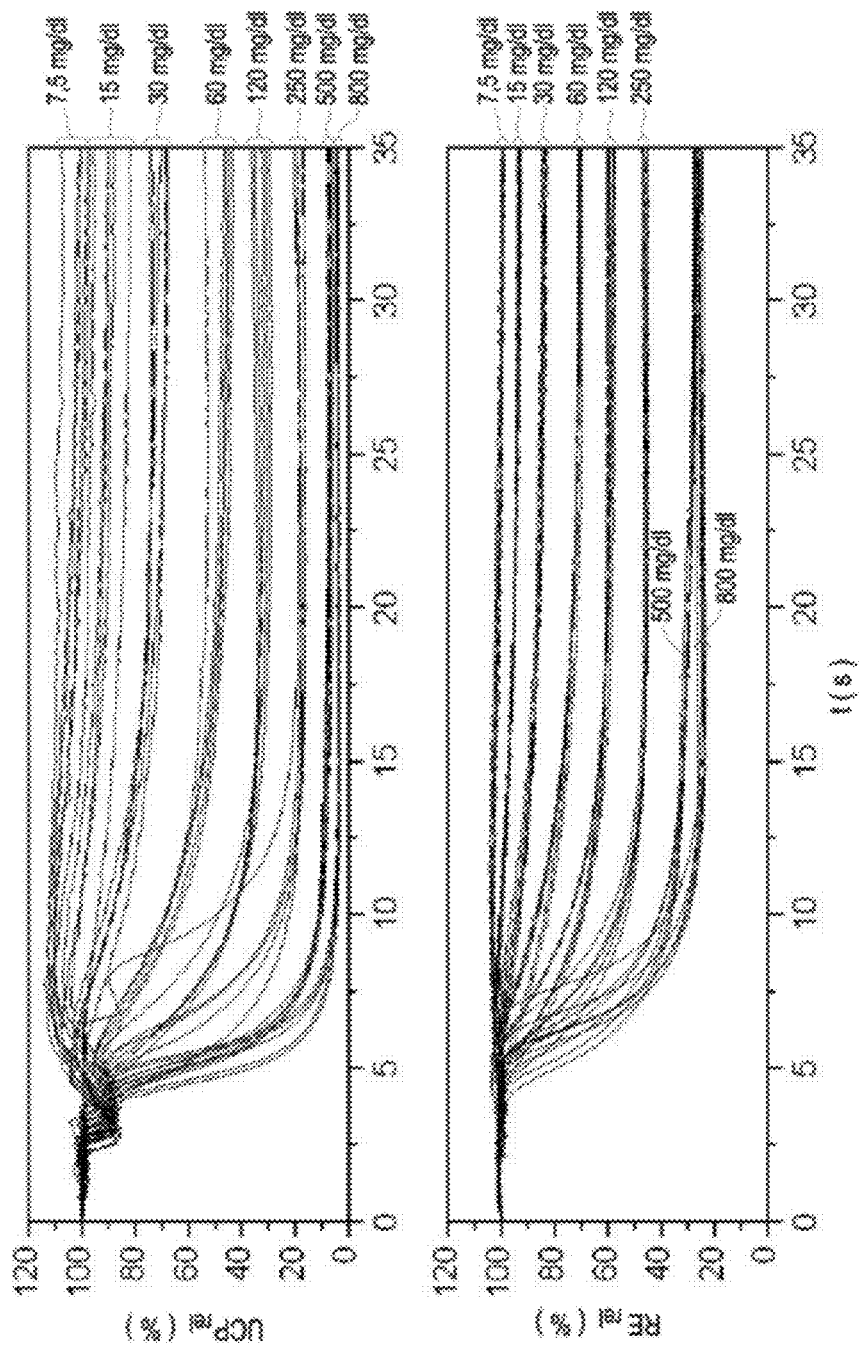

FIG. 4 shows kinetic curves of test strips in the presence of various amounts of glucose portrayed as relative signals for UCP-based measurement (upper panel) and re-emission of a standard PMo dye (lower panel) Glucose concentrations are indicated. Y-Axes: $UCP_{rel}$: relative UCP-Signal (%) and $RE_{rel}$: relative re-emission (%); X-Axes: t: Timepoints (s).

Figure 5:
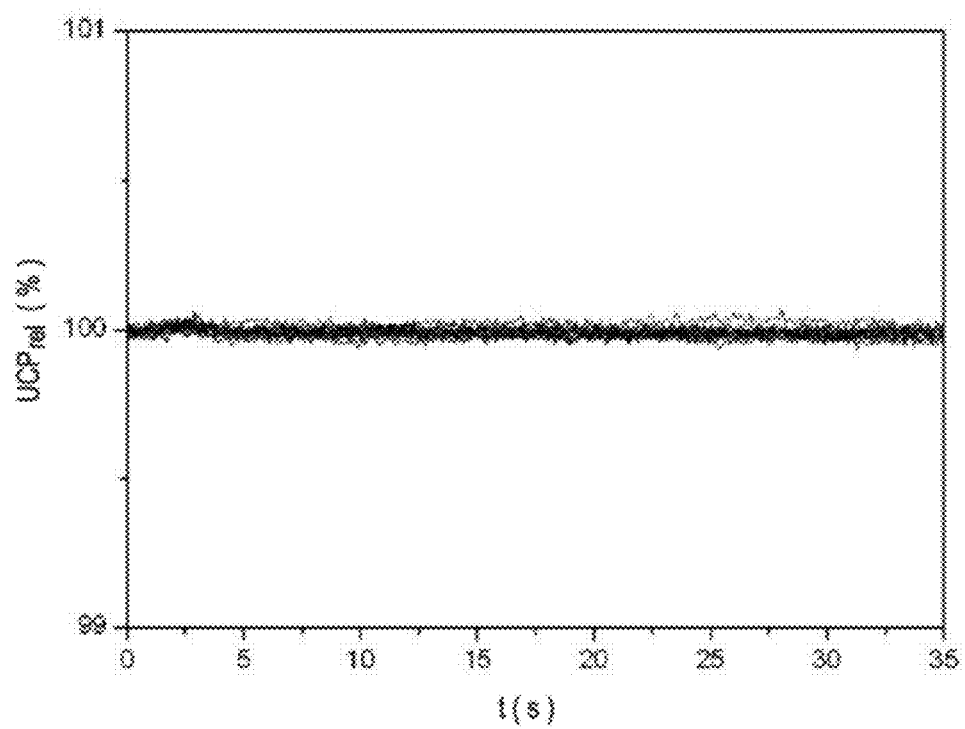

FIG. 5 shows kinetic curves of test strips lacking UCPs in the presence of various amounts of glucose portrayed as relative signals for UCP-based measurement. Y-Axis: $UCP_{rel}$: relative UCP-Signal (arbitrary units) and $RE_{rel}$: relative RE-Emission (%); X-Axes: t: Timepoints (s).

Figure 6:
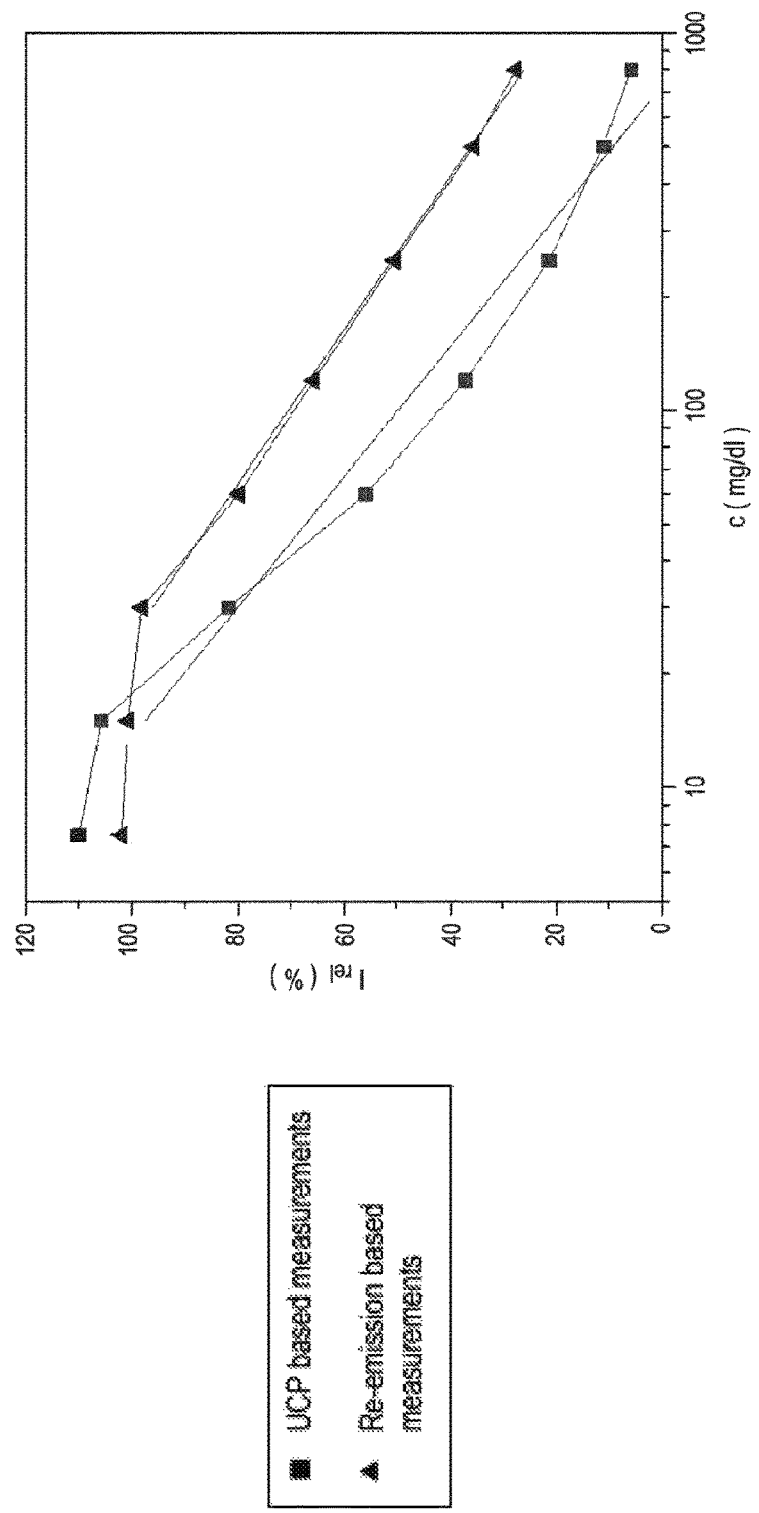

FIG. 6 shows standard curves for UCP-based and re-emission based measurements and their corresponding linear regression lines. $R^2$ values are 0.96 for UCP-based measurement and 0.997 for re-emission based measurement. Y-Axis: $I_{rel}$: mean relative signal (%), endpoint was at <2% slope; and CV %: coefficient of variation. X-Axis: c: glucose concentration (mg/dl).

Figure 7:
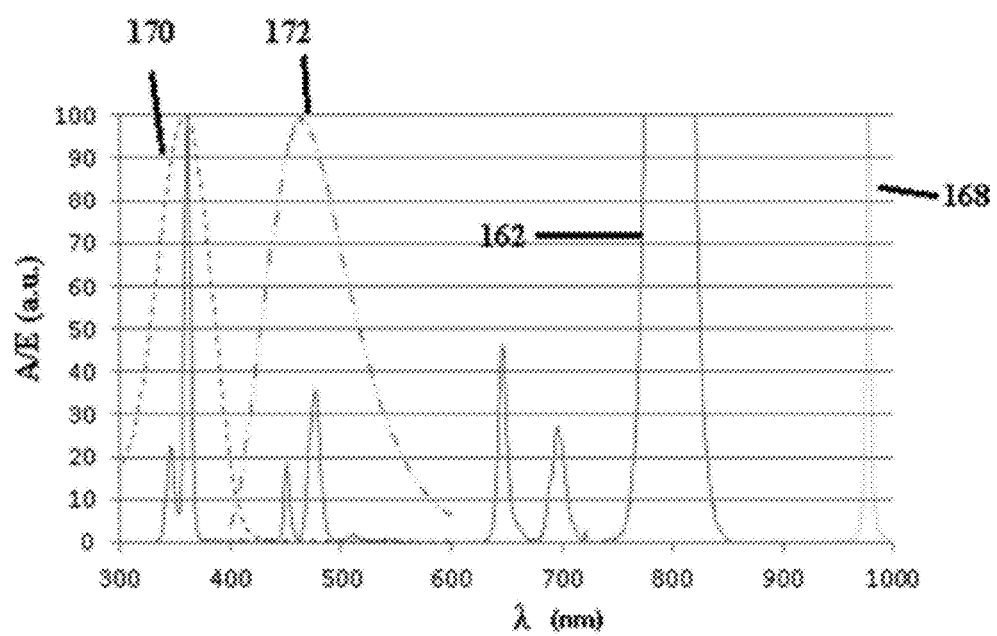

FIG. 7 shows spectra of the IR laser, of UV-UCP excitation and emission, and cNADH absorption and emission. 168: UCP excitation; 162: UCP emission; 170: cNADH absorption; 172: cNADH emission. X-Axis: $\lambda$: wavelength (nm). Y-Axis: A: Absorption, E: Excitation (both: arbitrary units).

Figure 8:
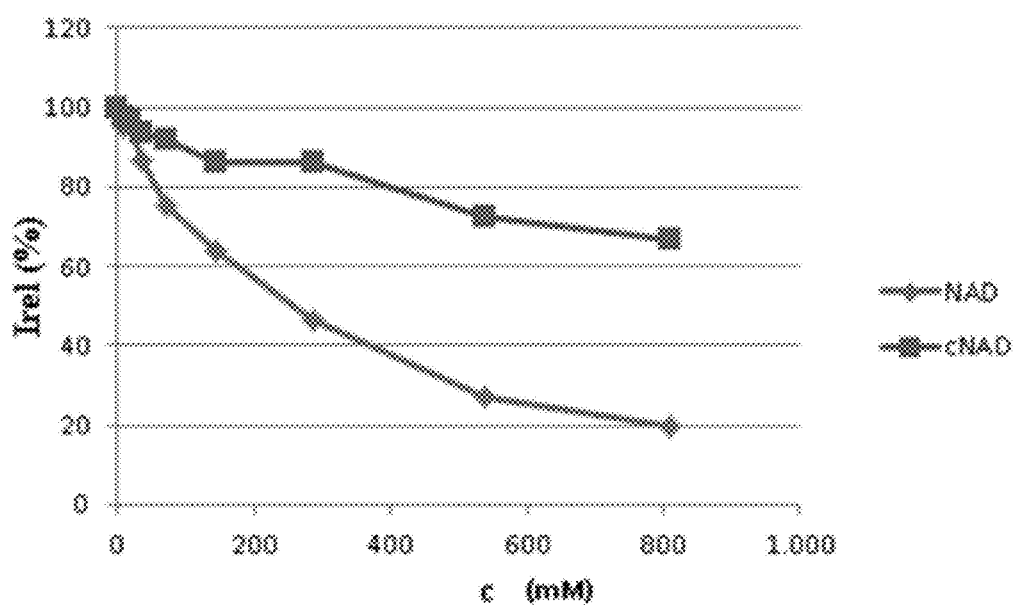

FIG. 8 relative signal intensities at 365 and 800 nm of UV-UCPs in assay mixtures comprising various amounts of glucose. X-Axis: c: glucose concentration (mM); Y-Axis: $I_{rel}$: relative intensity (=signal after addition of glucose/signal before addition of glucose).

Figure 9:
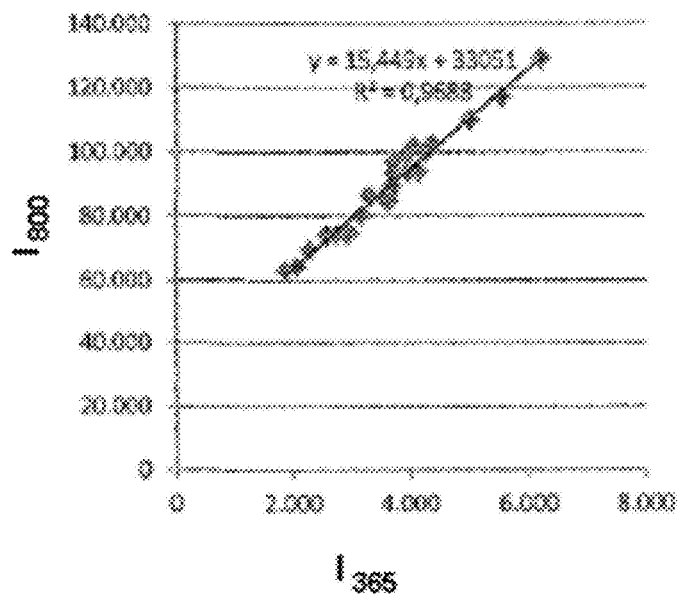

FIG. 9 correlation between the signals at 365 nm and at 800 nm on a glucose test strip comprising UV-UCP before addition of glucose.

Figure 10:
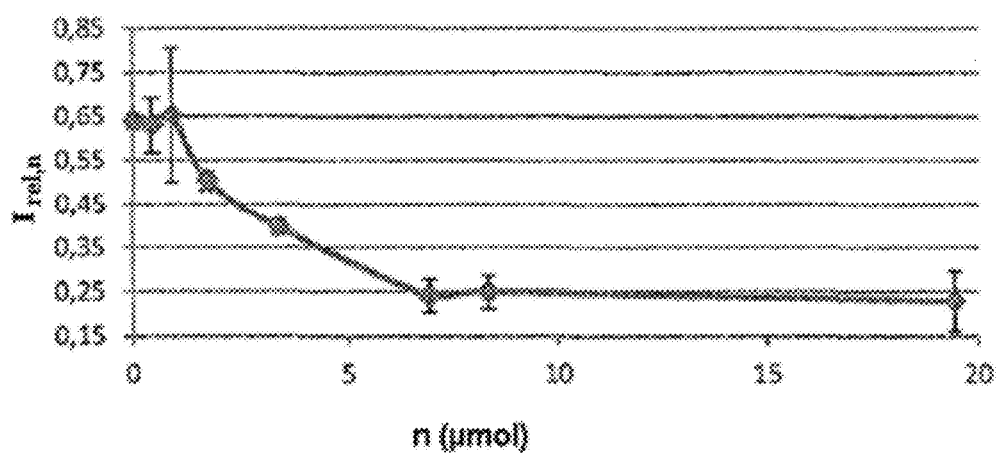

FIG. 10 relative normalized signal intensities detectable from a UV-UCP test strip in the presence of various amounts of glucose. X-Axis: n: amount of glucose per test strip (µmol); Y-Axis: $I_{rel,n}$: relative normalized signal intensity (=(signal at 365 nm after addition of glucose)/(signal at 800 nm after addition of glucose)/(signal at 365 nm before addition of glucose/signal at 800 nm before addition of glucose).

Figure 11:
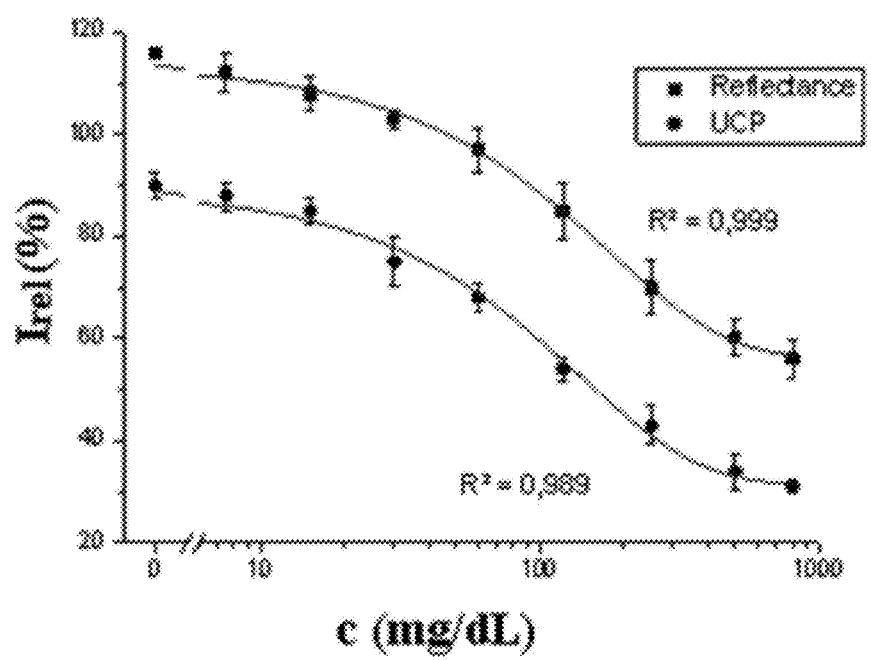

FIG. 11 relative signal intensities detectable from a UV-UCP test strip (graph UCP) in the presence of various amounts of glucose dissolved in $D_2O$, compared to conventional cNAD test strips (graph "reflectance"). X-Axis: c: glucose concentration in the sample applied to the test strip; Y-Axis: $I_{rel}$: relative signal intensity.

DETAILED DESCRIPTION OF THE EMBODIMENTS

Figure 1:
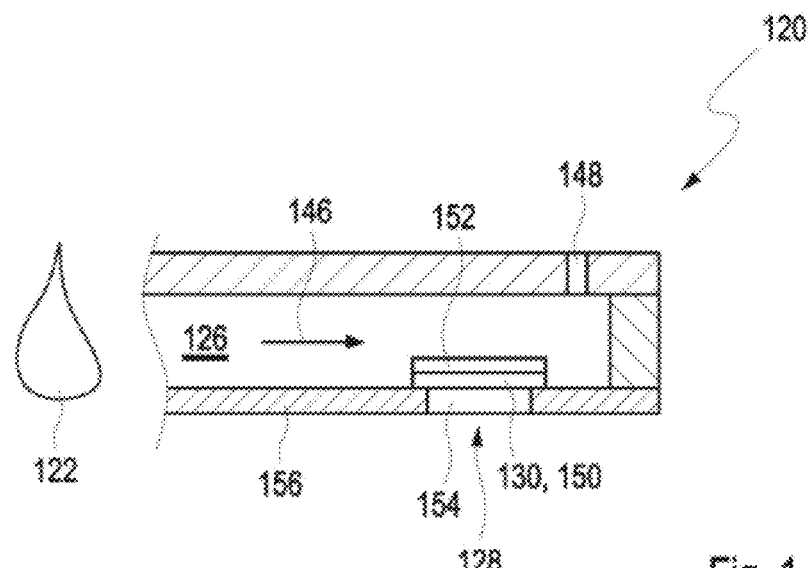
FIG. 1 shows a schematic cross-sectional view of a test element for use in the test system according to FIG. 1.

In FIG. 1, a cross-sectional view of an exemplary embodiment of a test element 120 is depicted. In this exemplary embodiment, the test element 120 is designed as a test strip. However, additionally or alternatively, other types of test elements 120 may be used, such as test tapes and/or test discs.

The test element 120, as outlined above, comprises at least one test field 128 and at least one capillary element 126. The capillary element 126 is adapted to guide the sample 122 of the body fluid across the test field 128 in a flow direction 146. Thus, the capillary element 126 may suck the sample 122 over the test field 128 by capillary forces. For improving the capillary forces, the test element 120 may further comprise one or more venting openings 148.

The test field 128 comprises at least one detection comprising the at least one detector matrix 130. The test field 128 may further comprise one or more additional layers, such as at least one separation layer 152 covering the detection layer 150 on the side facing the capillary element 126. The separation layer 152 may comprise one or more pigments, preferably inorganic pigments, such as an inorganic oxide, which may provide a white optical background for optical measurement. Further, the separation layer 152 may be adapted for separating off at least one particular component contained in the body fluid.

The test element 120 comprises at least one detection window in a substrate 156, through which a change of optical properties in the test field 128 may be detected by using the detector 132. It shall be noted that, in the embodiment depicted in FIG. 2, an optical test element 120 is depicted, in which the detector matrix 130 is adapted to change at least one optical property in the presence of the analyte to be detected.

Figure 2:
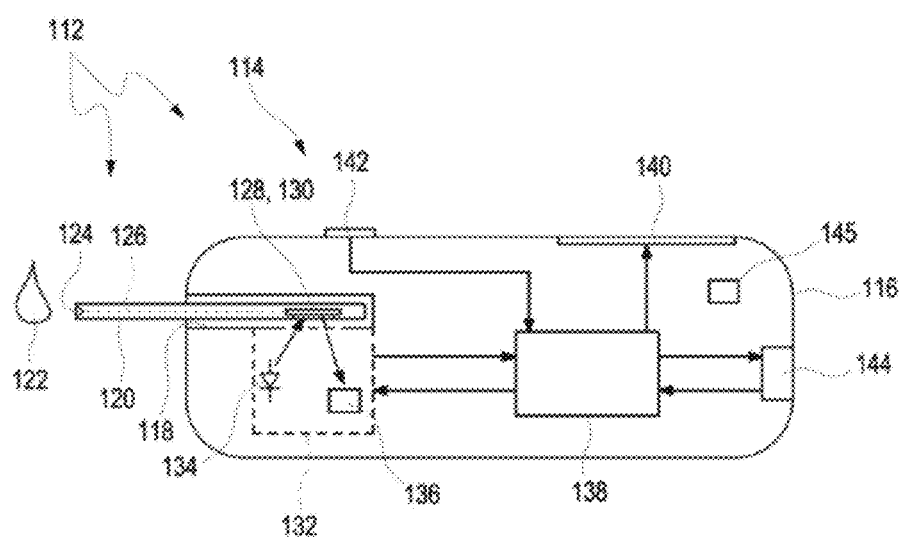
FIG. 2 shows a cross-sectional view of an exemplary embodiment of a test system and a test device according to the present invention.

In FIG. 2, a cross-sectional view of an embodiment of a test device 112 and a test system 114 according to the present invention is depicted. The test device 112, preferably, is embodied as a hand-held device. The test device 112 preferably comprises a casing 116, which may have a volume of less than 1000 cm³, preferably of less than 500 cm³, in order to be carried by a person. The test device 112 comprises a receptacle 118 for receiving a test element 120, which, besides the test device 112, forms a component of the test system 114. The receptacle is adapted to locate the test element 120 in at least one application position in which a sample 122 of the body fluid is applicable to the test element 120, such as to an application opening 124 of a capillary element 126, which will be explained in further detail below. The test element 120 comprises at least one test field 128 having at least one detector matrix 130 adapted to change at least one optical property in the presence of an analyte to be detected by the test system 114, such as glucose.

The test device 112 further comprises a detector 132 which, in this specific embodiment, comprises at least one light source 134 for illuminating the test field 128 and at least one optically sensitive element 136 adapted to measure detection light emitted and/or transmitted and/or reflected from the test field 128.

The test device 112 further comprises at least one evaluation unit 138 which is adapted to determine the concentration of the analyte by using an evaluation algorithm. The evaluation unit 138 preferably may be or may comprise at least one data processing device, such as at least one computer and/or at least one application-specific integrated circuit. As an example, the evaluation unit 138 may comprise a microcomputer. Further, the evaluation unit 138 may comprise one or more further elements, such as at least one data storage device and/or other components. The evaluation unit 138 is unidirectionally or bidirectionally connected to the detector 132, such as for receiving measurement values from the detector 132. Further, the evaluation unit 138 may be adapted to control the overall functionality of the test device 112, such as for controlling the measurement process performed by the detector 132.

The test device 112 may further comprise one or more human-machine-interfaces, such as at least one display 140 and/or at least one control element 142, such as at least one push button. The elements 140, 142 may also be connected to the evaluation unit 138. The test device 112 may further comprise one or more additional sensors for detecting one or more ambient parameters, such as one or more temperature sensors 145 adapted for determining an ambient temperature. As outlined above, these one or more ambient parameters may be used by the evaluation unit 138 for choosing an appropriate algorithm. The test device 112 may further comprise at least one electronic interface 144, for unidirectional and/or bidirectional exchange of data and/or commands with one or more external devices, such as a wireless and/or a wire-based interface.

In the following, several measurements will be shown for demonstrating that detector matrices comprising UCP can be used to determine the concentration of an analyte, in particular glucose, in a sample.

EXAMPLES

I. UCPs

Example 1: Materials and Methods

Commercially available UCP particles (Honeywell Lumilux Green UC 2, Honeywell Specialty Chemicals Seelze GmbH) were mixed with polyacrylic acid (poly(acrylic acid, sodium salt), Sigma-Aldrich) and then embedded in to the bottom chemical layer by mixing them with the standard coating mixture as described below. These particles were composed of $Y_2O_2S$:Yb,Er and were excited with an infrared radiation (980 nm). The test strips were then used to investigate the correlation between the detected UCP emission as a function of glucose concentration under infrared laser excitation.

Example 2: Coating of Test Strips

The coating mixture of the chemical layers was as follows (components are in aqueous solution):
Bottom layer: 0.99 g/m² L-glycerol-3-phosphate-di-sodium; 1.89 g/m² HCl; 0.38 g/m² Keltrol F; 0.070 g/m² TEACl; 0.19 g/m² Mega 8; 0.025 g/m² Geropon T77; 0.98 g/m² PVP 2500; 5.8 g/m² Transpafill; 11.1 g/m² Propiofan; 0.11 g/m² N,N-bis-hydroxyethyl-p-nitrosoanilin; 0.33 g/m² PMo; 0.0037 g/m² PQQ disodium salt; 0.27 g/m² mut Q-GDH2; 0.80 g/m² RbOH; 0.020 g/m² $CaCl_2$*2 $H_2O$; 0.020 g/m² $K_3[Fe(CN)_6]$; 0.083 g/m² NaOH; 1.0 g/m² 2-methyl-2-butanol; 8.15 g/m² UCP; 0.40 g/m² PAA. pH 6.85.

Top layer: 1.4 g/m² Gantrez S97; 0.29 g/m² NaOH; 0.55 g/m² TEACl; 0.33 g/m² Mega 8; 0.090 g/m² Geropon T77; 1.8 g/m² PVP2500; 1.9 g/m² silicic acid FK320DS; 18 g/m² $TiO_2$; 11 g/m² Propiofan; 0.080 g/m² BM 31.1008; 2.3 g/m² PMo; 0.050 g/m² $CaCl_2$*2 $H_2O$; 0.082 g/m² LiOH; 1.0 g/m² 2-methyl-2-butanol. pH 6.75.

Coating was performed on Pocalon N343 EM (125 µm thick, Lonza, Basel, Germany). Bottom layer coating thickness was 113 µm and top layer 54 µm.

Example 3: Measurements

The emission of the UCP was monitored with a J&M TIDAS S DAD—spectrometer by recording the detected spectra with 200 ms integration time and 250 ms datapoint interval. The IR excitation source was a 100 mW continuous wave diode laser system (LRD-0980-PFR, Laserglow Technologies, Toronto, Canada) that was attenuated down to 1.6 mW. After the excitation and recording of the spectra were started, a 5 µl sample of glucose solution was introduced to the test strip.

From the recorded spectra the emission intensity from 650-690 nm in different timepoints was integrated and each of the values was compared to the initial one to obtain the relative intensity in different timepoints. These values were then used to determine the point on the kinetic curve, where the slope is <2%/s, that was used as a reaction endpoint for the glucose concentration in question. The average values of these endpoints (5 replicates) were then plotted as a function of glucose concentration. The same test strips were also used for a reference measurement that was performed with the current technique by observing the relative amount of re-emitted light at 660 nm.

Example 4: Spectra

The spectra of the IR laser, UCP emission and the absorption of the PMo dye are presented in FIG. 3. The 980 nm laser band is used to excite the UCP particles in the test strips that emit around 550 and 660 nm. The PMo dye has a broad absorption spectrum overlapping the UCP emission but also with the laser line.

Example 5: Results

Kinetic curves obtained are displayed in FIG. 4 for the UCP (FIG. 4A) and re-emission based measurement (FIG. 4B). Key findings are an increased dynamic signal range and an increase in the relative signal with low glucose concentrations in the UCP signals in comparison to re-emission measurement.

Test strips that did not contain any UCP did not produce any detectable signal under IR excitation. The kinetic data from these test strips show that there is also no change in the relative signal over time as glucose sample is applied (FIG. 5).

The code curves obtained from UCP-based and re-emission measurements are presented in FIG. 6. As can be derived from FIG. 6, the UCP-based measurement has much wider relative signal range as compared to the traditional re-emission based measurement. Specifically, the relative signal difference between values measured at 7.5 and at 500 mg/dl glucose was 98.8% for the UCP-based measurement, but only 66.3% for the traditional re-emission based measurement.

II. UV-UCPs

Example 6: UV-Emitting UCPs in Glucose Measurement

FIG. 7 shows the emission spectrum of UCP particles consisting of Na/KYF$_4$:Yb, Tm (20 mol % K$^+$) and shows a strong emission around 360 nm after laser excitation at 980 nm. This UV-emission is conveniently located in the same region where the indicators and redox cofactors NADH and cNADH have their absorption maxima. There are also emission lines in the 800-900 nm region that are not affected by the indicator absorption or emission, and can therefore be used as an internal control to compensate fluctuations caused by the excitation source.

A glucose assay was conducted using the above-mentioned UV-UCP-particles together with NAD or cNAD and glucose dehydrogenase enzyme in a buffered aqueous solution on microtitre wells. Each well contained 50 ng of UCP, 1.88 µmol of indicator (NAD or cNAD) and 1 µg enzyme in 200 µl volume. The UV emission from the UCPs was measured in the beginning at two wavelengths (365 and 800 nm UCP emission) to acquire the zero-level signal. After this, a 10 µl sample of glucose was added, incubated for 15 min and measured again. The results were then calculated by comparing the emission intensities in each sample concentration to the respective zero-signal intensity. FIG. 8 shows the relative signals calculated for each of the glucose concentrations.

As FIG. 8 indicates, the emission at 365 nm of the UCP decreases as the indicator is reduced due to the addition of glucose, whereas the emission at 800 nm remains unaffected. cNAD was used in the same concentration as NAD; since cNAD has a different equilibrium in the reaction, the decrease in UCP emission is less pronounced.

Example 7: UV-UCP in Glucose Test Strips

For these experiments, the same UV-UCP as in Example 6 were used in a coating mixture having the composition indicated below. These particles are quenched by water, such that in the presence of water, a part of the emission below 800 nm is lost. In order to show that the basic principle is working, water was removed from the strips by drying and then the final signal was measured.

The coating mixture of the chemical layers was as follows (components are in aqueous solution):

Bottom layer: 2.5 g/m$^2$ Sipernat FK 320DS; 0.20 g/m$^2$ poly(acrylic acid, sodium salt); 0.38 g/m$^2$ Gantrez S97; 1.0 g/m$^2$ Propiofan 70D; 0.040 g/m$^2$ Geropon T77; 0.26 g/m$^2$ Na/KPO$_4$; 1.60 g/m$^2$ cNAD-Na and 0.80 g/m$^2$ GlucDH2. The pH of the coating mixture adjusted to 7.5.

Top layer: 16.5 g/m$^2$ ZrO$_2$ TZ-3YS; 0.35 g/m$^2$ poly(acrylic acid, sodium salt); 1.30 g/m$^2$ Gantrez S97; 2.17 g/m$^2$ Propiofan 70D; 6 g/m$^2$ UCP and 0.04 g/m$^2$ Geropon. pH=7.5.

Coating was performed on Bayfol CR210 (125 µm thick, Bayer MaterialScience AG, Germany). Bottom layer coating thickness was 50 µm and top layer 100 µm.

The UV-UCPs were coated in the upper layer of cNAD test strips. The emission of UCPs without glucose was first measured under an infrared laser excitation with a power of 100 mW, providing proof that the emissions at 365 nm and at 800 nm are linearly correlated (FIG. 9). After this, 5 µl of a glucose sample were introduced onto the strips, with glucose concentrations varying from 0 to 800 mg/ml (0-19.4 µmol of glucose per strip) with three replicates for each concentration. The strips were then dried in 50° C. for 20 minutes in order to remove water from the strips. After drying, the strips were measured as described above.

The UV-emission was first normalized calculating the ratio with the emission measured at 800 nm. The normalized signals from before and after the addition of glucose and drying were then compared to calculate the relative signal. This was finally plotted as a function of the amount of glucose introduced to the test strip (FIG. 10), showing that the detected UCP emission is inversely correlated with the amount of glucose introduced to the test strip.

Example 8: UV-UCP in Glucose Test Strips with D$_2$O

For these experiments, the same test strips as in Example 7 were used. As another way of avoiding quenching by water, D$_2$O was used as a solvent for dissolving glucose. Measurements were performed as described in Example 7, however, without drying the test strips after application of glucose solutions. As shown in FIG. 11, correlation between the relative signal measured and the amount of glucose applied in UV-UCP test strips ("UCP") is as good as in conventional measurement of blood glucose with cNAD test strips ("reflectance").

The work leading to this invention has received funding from the European Research Council under the European Union's Seventh Framework Programme (FP7/2007-2013)/ERC grant agreement no. 264772 (CHEBANA).

LIST OF REFERENCE NUMBERS 112 test device
114 test system
116 casing
118 receptacle
120 test element
122 sample
124 application opening
126 capillary element
128 test field
130 detector matrix
132 detector
134 light source
136 optically sensitive element
138 evaluation unit
140 display
142 control element
144 interface
145 temperature sensor
146 flow direction
148 venting opening
150 detection layer
152 separation layer
154 detection window
156 carrier element (support)
160 light reflected from a conventional teststrip in the presence of glucose
162 UCP emission
164 light reflected from a conventional teststrip in the absence of glucose
166 IR-laser spectrum
168 UCP excitation 170 cNADH absorption
172 cNADH emission

The invention claimed is:

1. A detector matrix for detecting at least one analyte in a sample comprising (i) at least one enzyme active in the presence of said at least one analyte and (ii) at least one indicator reagent changing at least one optical property dependent on the activity of said enzyme, wherein the indicator reagent is homogenously distributed within said detector matrix, wherein said detector matrix further comprises (iii) UV-emitting up-converting phosphor particles.

2. The detector matrix of claim 1, wherein the optical property is a property selected from the group consisting of light absorption, light emission, and light remission.

3. The detector matrix of claim 1, wherein the detector matrix further comprises (iv) at least one redox cofactor and (v) an agent capable of eliciting a change in at least one optical property of said at least one indicator reagent in the presence of redox equivalents, and wherein the enzyme is a dehydrogenase.

4. The detector matrix of claim 3, wherein the dehydrogenase is a glucose dehydrogenase.

5. The detector matrix of claim 1, wherein the UV-emitting up-converting phosphor particles comprise $NaYF_4$: $Yb^{3+}$, $Tm^{3+}$, doped with $K^+$ and/or $Sc^{3+}$.

6. A test element for detecting at least one analyte in a sample comprising the detector matrix of claim 1 or comprising the components of the detector matrix of claim 1.

7. The test element of claim 6, wherein said test element is adapted for detecting said at least one analyte by irradiating said test element at the sample application side and by detecting emission at the side opposite to said sample application side.

8. A test device comprising at least one receptacle for a test element according to claim 6 and a detector comprising
 (i) at least one light source adapted for illuminating the test element with light having a first wavelength $\lambda_1$, and
 (ii) at least one optically sensitive element adapted for detecting light having a second wavelength $\lambda_2$, emitted by the test element, the second wavelength being a lower wavelength as compared to the first wavelength, wherein said test device is adapted for through-sample measurement.

9. The test device of claim 8, wherein at least one light source is adapted for illuminating the test element from the sample application side and wherein at least one optically sensitive element is adapted for detecting light emitted by the test element from the side opposite to said sample application side.

10. A test system comprising
 (A) a test device comprising at least one receptacle for a test element according to claim 6 and a detector comprising
  (i) at least one light source adapted for illuminating the test element with light having a first wavelength $\lambda_1$, and
  (ii) at least one optically sensitive element adapted for detecting light having a second wavelength $\lambda_2$, emitted by the test element, the second wavelength being a lower wavelength as compared to the first wavelength,
 wherein said test device is adapted for through-sample measurement;
 and said test system further comprising
 (B) the test element of claim 6.

11. The detector matrix of claim 1, wherein the redox cofactor is NAD or a derivative thereof.

12. The detector matrix of claim 1, wherein the UV-emitting up-converting phosphor particles are coated with one or more inert and/or hydrophilic coatings.

* * * * *